United States Patent [19]

Montagnier et al.

[11] Patent Number: 5,830,641
[45] Date of Patent: Nov. 3, 1998

[54] IN VITRO DIAGNOSTIC ASSAYS FOR THE DETECTION OF HIV-1 OR HIV-2 EMPLOYING VIRAL-SPECIFIC ANTIGENS AND ANTIBODIES

[75] Inventors: Luc Montagnier, Le Plessis Robinson; Denise Guetard, Paris; Marc Alizon, Paris; François Clavel, Paris; Mireille Guyader, Paris; Pierre Sonigo, Paris, all of France

[73] Assignee: Institut Pasteur, Paris, France

[21] Appl. No.: 214,299

[22] Filed: Mar. 17, 1994

Related U.S. Application Data

[62] Division of Ser. No. 75,020, Jun. 11, 1993, abandoned, which is a continuation of Ser. No. 792,524, Nov. 18, 1991, abandoned, which is a division of Ser. No. 462,908, Jan. 10, 1990, Pat. No. 5,066,782, which is a continuation of Ser. No. 150,645, filed as PCT/FR87/00025 Jan. 22, 1987, abandoned, which is a continuation-in-part of Ser. No. 3,764, Jan. 16, 1987, Pat. No. 5,051,496, which is a continuation-in-part of Ser. No. 933,184, Nov. 21, 1986, abandoned, which is a continuation-in-part of Ser. No. 916,080, Oct. 8, 1986, abandoned, and a continuation-in-part of Ser. No. 835,228, Mar. 3, 1986, Pat. No. 4,839,288.

[30] Foreign Application Priority Data

| Jan. 22, 1986 | [FR] | France | 86 00910 |
| Jan. 22, 1986 | [FR] | France | 86 00911 |
| Feb. 6, 1986 | [FR] | France | 86 01635 |
| Feb. 13, 1986 | [FR] | France | 86 01985 |
| Mar. 18, 1986 | [FR] | France | 86 03881 |
| Mar. 24, 1986 | [FR] | France | 86 04215 |

[51] Int. Cl.⁶ ............................................. C12Q 1/70
[52] U.S. Cl. .................. 435/5; 435/7.1; 530/389.4; 424/139.1; 424/159.1; 424/188.1
[58] Field of Search ....................... 435/5; 436/808; 530/350, 388.35, 389.4; 424/188.1, 208.1

[56] References Cited

U.S. PATENT DOCUMENTS

| 4,629,783 | 12/1986 | Cosand | 530/324 |
| 4,839,288 | 6/1989 | Montagnier et al. | 435/235 |
| 4,877,725 | 10/1989 | Neurath et al. | 435/5 |
| 5,051,496 | 9/1991 | Alizon et al. | 530/324 |
| 5,066,782 | 11/1991 | Montagnier et al. | 530/324 |
| 5,079,342 | 1/1992 | Alizon et al. | 530/324 |
| 5,670,309 | 9/1997 | Norrby et al. | 435/5 |

FOREIGN PATENT DOCUMENTS

| 0 316 695 B1 | 3/1993 | European Pat. Off. |
| WO 85/04897 | 11/1985 | WIPO |

OTHER PUBLICATIONS

Strongin, W., 1993, "Sensitivity, Specificity, and Predictive Value of Diagnostic Test: Definitions and Clinical Applications", in Laboratory Diagnosis of Viral Infections, Lennette, E., ed., Marcel Dekker Inc., New York, pp. 211–219.

Norrby et al. (1988, "Type–specific site–directed human immunodeficiency virus serology", in Vaccines 88, Cold Spring Harbor Laboratory, pp. 335–339).

(List continued on next page.)

*Primary Examiner*—Donald E. Adams
*Assistant Examiner*—Jeffrey S. Parkin
*Attorney, Agent, or Firm*—Finnegan, Henderson, Farabow, Garrett & Dunner, L.L.P.

[57] ABSTRACT

The invention relates to a new class of retroviruses, designated by HIV-2, of which samples have been deposited to the ECACC under numbers 87.01.1001 and 87.01.1002 and to the NCIB under numbers 12.398 and 12.399.

It relates also to antigens capable to be obtained from this virus, particularly proteins p12, p16, p26 and gp140. These various antigens can be used for the diagnosis of the disease, especially by contacting these antigens with a serum of a patient submitted to the diagnosis.

It relates to immunogenic compositions containing more particularly the glycoprotein gp140. Finally it concerns nucleotidic sequences, which can be used especially as hybridization probes, derived from the RNA of HIV-2.

24 Claims, 7 Drawing Sheets

OTHER PUBLICATIONS

Tedder et al. (1988, "Envelope cross–reactivity in western blot for HIV–1 and HIV–2 my not indicate dual infection", The Lancet 2:927–931.

Hunt et al., 1990, "Discrimination between HIV–1 and HIV–2–seropositive individuals using mouse monoclonal antibodies directed to HIV transmembrane proteins", AIDS Res. Human Retro. 6:883–898.

Laurence, J., "Update: HIV–1 gene nomenclature", AIDS Res. Hum. Retro. 4:vii–viii (1988).

Gallo et al., "HIV/HTLV gene nomenclature", Nature (London) 333:504 (1988).

Clavel et al., "Isolation of a new human retrovirus from West African patients with AIDS", Science 233:343–347 (1986).

L. Stryer, *Biochemistry,* pp. 761–763 (W. H. Freeman and Company, San Francsico, 1975).

Clavel et al., "Molecular Cloning and Polymorphism of the Human Immune Deficiency Virus Type 2", *Nature,* 324, 691–694 (1986).

Guyader et al., "Genome Organization and Transactivation of the Human Immunodeficiency Virus Type 2", *Nature,* 326, 662–669 (1987).

Wang et al., "Detection of Antibodies to Human T–lymphotropic Virus Type III by Using a Synthetic Peptide of 21 Amino Acid Residues Corresponding to a Highly Antigenic Segment of gp41 Envelope Protein", *Proc. Natl. Acad. Sci., USA,* 83, 6159–6163 (1986).

Chakrabarti et al., "Sequence of Simian Immunodeficiency Virus from Macaque and Its Relationship to Other Human and Simian Retroviruses", *Nature,* 328, 543–547 (1987).

Kanki et al., "Serologic Identification and Characterization of a Macaque T–lymphotropic Retrovirus Closely Related to HTLV–III," *Science,* 228, pp. 1199–1201 (1985).

Clavel et al., "Isolation of a New Human Retrovirus from West African Patients With AIDS," *Science,* 233, 343–346 (1986).

Clavel et al., "LAV Type II: A Second Retrovirus Associated With AIDS In West Africa," *C.R. Acad. Sc. Paris,* Serie III, 302, pp. 485–488 (1986).

Klatzmann et al., "T–lymphocyte T4 Molecule Behaves As The Receptor For Human Retrovirus LAV," *Nature,* 312, pp. 767–768 (1984).

Daniel et al., "Isolation of T–cell Tropic HTLV–III–like Retrovirus from Macaques," *Science,* 228, pp. 1201–1204 (1985).

Barin et al., "Serological Evidence For Virus Related To Simian T–lymphoctropic Retrovirus III in Residents of West Africa," *The Lancet,* pp. 1287–1389 (Dec. 21/28, 1985).

Sandstrom et al., "Antiviral Therapy In AIDS Clinical Pharmacological Properties and Therapeutic Experience to Date," *Drugs,* 34, pp. 372–390 (1987).

Mitsuya et al., "Protection of T Cells Against Infectivity and Cytopathic Effect of HTLV–III In Vitro," Retroviruses in Human Lymphoma/Leukemia, M. Miwa et al., eds., pp. 277–288 (Japan Science Press, Tokyo, 1985).

```
          10        20        30        40        50        60        70        80        90       100
GTGGAAGGCGAGACTGAAAGCAAGAGAGGAATACCATTTAGTTAAAGGACAGGAACAGCTATACTTGGTCAGGGCAGGAAGTAACTAACAGAAACAGCTGAG
                    MNLI                                           ALUI                    MAEIII  PVUI
                                                                                                   ALUI
                                                                                                      DDEI 110       120       130       140       150       160       170       180       190       200
ACTGCAGGGACTTTCCAGAGAAGGGGCTGTAACCAAGGGAGGAGACATGGGAGGAGCTGGTGGGGAACGCCTCATATTCTCTGTATAATATACCCGCTGCTTG
PSTI            MAEIII MNLI    NLAIII  ALUI                  MNLI                        BBVI
                STYI           MNLI                                                      FNU4HI
                                                                                         TH111II 210       220       230       240       250       260       270       280       290       300
CATTGTACTTCAGTCGCCTCTGCCGGAGAGGCTGGCAGATTGAGCCCTGAGGATCTCTCCAGCACTAGACGGATGAGCCTGGGTGCCCTGCTAGACTCTCA
RSAI            MNLI                 BANII   MNLI   XHOII              MAEI      APYI BSP1286 MAEI  HPHI
                                     BSP1286        DPNI                         BSTNI              HINFI
                                     APYI           MBOI                         ECORII
                                     BSTNI          NDEII                        SCRFI
                                     ECORII        SAUIIIA                       BANI
                                     SCRFI 310       320       330       340       350       360       370       380
CCAGCACTTGGCCGGTGCTGGCAGACGGCCCCACGCTTGCCTGCTTAAAAACCTTCCTTAATAAAGCTGCAGTAGAAGCA
HAEIII          HAEIII                                                  ALUI
HAPII           SAU96A                                                  BBVI
HPAII                                                                   FNU4HI
MSPI

FIG. 6
```

IN VITRO DIAGNOSTIC ASSAYS FOR THE DETECTION OF HIV-1 OR HIV-2 EMPLOYING VIRAL-SPECIFIC ANTIGENS AND ANTIBODIES

This is a division of application Ser. No. 08/075,020, filed Jun. 11, 1993, now abandoned, which is a continuation of application Ser. No. 07/792,524, filed Nov. 18, 1991, now abandoned, which is a divisional of application Ser. No. 07/462,908, filed Jan. 10, 1990, now U.S. Pat. No. 5,066, 782, which is a continuation of application Ser. No. 07/150, 645, filed as PCT/FR87/00025, Jan. 22, 1987, now abandoned, which is a continuation-in-part of application Ser. No. 07/003,764, filed Jan. 16, 1987, now U.S. Pat. No. 5,051,496, which is a continuation-in-part of application Ser. No. 06/933,184, filed Nov. 21, 1986, now abandoned, which is a continuation-in-part of application Ser. No. 06/916,080, filed Oct. 6, 1986, now abandoned, and a continuation-in-part of application Ser. No. 06/835,228, filed Mar. 3, 1986, now U.S. Pat. No. 4,839,288, issued Jun. 13, 1989.

The invention relates to a new class of viruses having the capacity to cause lymphadenopathies, which are then capable of being replaced by acquired immune deficiency syndrome (AIDS) in man. The invention also relates to antigens capable of being recognized by antibodies induced in man by this new class of virus. It also relates to the antibodies induced by antigens obtained from these viruses.

This invention relates, furthermore, to cloned DNA sequences possessing sequence analogy or complementarity with the genomic RNA of the abovementioned virus. It also relates to the methods for preparing these cloned DNA sequences.

The invention also relates to polypeptides containing amino acid sequences encoded by the cloned DNA sequences.

In addition, the invention relates to applications of these antigens to the in vitro diagnosis in man of potentials for certain forms of AIDS and, in respect of some of these antigens, to the production of immunogenic compositions and vaccinating compositions against this retrovirus. The invention likewised relates to the applications of the abovementioned antibodies for the same purposes and, for some of them, to their application to the production of active principle of drugs against these forms of human AIDS.

Finally, the invention relates to the application of the cloned DNA sequences, and of polypeptides obtained from these sequences, as probes in diagnostic kits.

The isolation and characterization of a first retrovirus, known as LAV, whose responsibility in the development of AIDS had been recognized, formed the subject of a description in a paper by F. BARRE-SINOUSSI et al. already in 1983 (Science, vol. 220, N° 45–99, 20, p. 868–871). Application of some extracts of this virus, and more especially of some of its proteins, to the diagnosis of the presence of antibodies against the virus was described more especially in European Patent Application n° 138.667. Since then, other similar strains and some variants of LAV have been isolated. Examples which may be recalled are those known by the names HTLV-III and ARV.

To apply the new rules of nomenclature published in Nature in May 1986, the retroviruses capable of inducing in man the abovementioned lymphadenopathies and AIDS will be given the overall designation "HIV", an abbreviation of the term "Human Immunodeficiency Virus". The subgroup of retroviruses formed by LAV and its variants was initially designated by the terms "LAV type I" or "LAV-I". The latter subgroup will be designated hereinafter HIV-1, it being understood that the term LAV will still be retained to denote that strain, among the strains of retrovirus (in particular LAAV, IDAV-4 and IDAV-2) belonging to the HIV-1 virus class which are described in the abovementioned European Patent Application 138,667, which was used in the comparative experiments described later, namely $LAV_{BRU}$, which was deposited with the Collection Nationale des Cultures de Micro-organismes (CNCM) (National Collection of Microorganism Cultures) of the Institut Pasteur de Paris, France, on 15th Jul. 1983 under $n_o$ I-232.

The new retrovirus which forms the subject of the present patent and the virus strains which are related to it and which are, like it, capable of multiplying in human lymphocytes, formerly known as. "LAV type II" or "LAV-II", are henceforward known as "HIV-2", it being understood that the designations of certain HIV-2 isolates described later will be followed by three letters which refer to the patients from whom they were isolated.

The "HIV-2" group can be defined as a group of viruses having in vitro a tropism for human T4 lymphocytes, and which have a cytopathogenic effect with respect to these lymphocytes when they multiply therein, and then either cause generalized and persistent polyadenopathies or one of the forms of AIDS. The HIV-2 retroviruses have proved to be different from the HIV-1 type viruses under the conditions mentioned later. Like these latter viruses, they are different from the other human retroviruses which are already known (HTLV-I and HTLV-II).

Although there is fairly wide genetic variability in the virus, the different HIV-1 strains isolated to date from American, European, Haitian and African patients have antigenic sites in common conserved on their principal proteins, i.e. core protein p25, envelope glycoprotein gp110 and transmembrane protein gp41-43. This relationship makes it possible, for example, for the prototype LAV strain to be used as a strain of antigens for detecting antibodies against all HIV-1 class viruses, in all people who carry them, regardless of their origin. This strain is hence currently used for detecting anti-HIV-1 antibodies in blood donois and patients, in particular by immunofluorescence and in particular by the technique known as ELISA, "Western Blot" (or immuno-imprinting) and "RIPA", an abbreviation for Radioimmunoprecipitation Assay.

However, in a serological study peformed with an HIV-1 lysate on patients who originated from West Africa, it was observed that some of them gave seronegative or very weakly positive reactions, whereas they showed clinical and immunological signs of AIDS.

The cultured lymphocytes of one of these patients were the source of a first HIV-2 retrovirus isolated, whose structure in electron microscopy and whose proteine profile in SDS gel electrophoresis show a resemblance to those of HIV-1. However, this new retrovirus HIV-2 possesses overall only a slight relationship to HIV-1, from the standpoint both of the antigenic homology of its proteins and of the homology of its genetic material.

This new retrovirus, or retroviruses having equivalent antigenic and immunological properties, can hence constitute sources of antigens for the diagnosis of infection by this virus and the variants which induce an AIDS form of the type which had been observed in the initial instances in African patients or in people who had spent time in Africa.

Typically, this virus was isolated from the blood, drawn in the presence of heparin, from a 28-year-old heterosexual patient who had never been transfused and who was not a drug addict. Since 1983, he had had substantial chronic diarrhoea, and substantial weight loss (17 kg) with intermittent fever. More recently, he had had Candida and Serratia infections, including an oesophageal candidiasis typical of AIDS.

This patient also had anaemia, cutaneous anergy, Lymphopenia and a T4 lymphocyte/T8 lymphocyte ratio of 0.15, with a T4 lymphocyte level of less than 100 per mm$^3$ of serum. His lymphocytes in culture did not respond to stimulation with phytohaemagglutinin and concanaval in A. This patient was also diagnosed as suffering from recurrent bacteriaemia due to *S. enteriditis*, cryptosporidioses, infections due to *Isospora belli* and cerebral toxoplasmoses.

This combination of signs was evidence of "complex symptoms linked with AIDS" or "ARC" (abbreviation for "AIDS-Related Complex"), of the type caused by HIV-1 virus. These various observations were also in conformity with the criteria applied by the Center of Disease Control (CDC) of Atlanta, USA.

The culturing of the lymphocytes from these patients and the isolation of the retrovirus were performed according to the technique already described for the isolation of HIV-1 in the paper by BARRE-SINOUSSI et al. and European Patent Application n° 84/401.834- 0.138.667. They are recalled briefly below. Lymphocytes stimulated for 3 days with phytohaemagglutinin (PHA) were cultured in RPMI 1640 culture medium to which 10% of foetal calf serum and 10 $^{-5}$M β-mecaptoethanol, interleukin-2 and anti-(human interferon α) serum are added.

The production of virus was followed by its reverse transcriptase activity. In the culture supernatant, the peak viral activity appeared at between day 14 and day 22, and then decreased. The decline and death of the cell culture followed. As with HIV-1, sections of lymphocytes infected with HIV-2 showed, in electron microscopy, virions which had reached maturity, and viral particles budding at the surface of the infected cells. The cell lines used for producing the cultures of these isolated viruses can be, depending on the case, cell lines of the HUT, CEM or MOLT type, or any immortalized lymphocyte Line bearing T4 receptors.

The virus was then propagated in cultures of lymphocytes from blood donors, and then in continuous lines of leukaemic origin, such as HUT 78. It was then characterized by its antigens and its nucleic acid as being substantially different from HIV-1. The virus was purified as described in the prior documents already mentioned. A first isolate of this virus was deposited with the CNCM on 19th Dec. 1985 under n° I-502. It was subsequently designated by the name LAV-II MIR. A second isolate was deposited with the CNCM on 21st Feb. 1986 under n° I-532. This second isolate has the reference name LAV-II ROD. These isolates will sometimes be referred to later simply as MIR or ROD.

In a general manner, the invention relates to any variant of the above viruses, or any equivalent virus (for example, such as HIV-2-IRMO and HIV-2-EHO, deposited with the CNCM on 19th Dec. 1986 under n°s I-642 and I-643, respectively), containing structural proteins which have the same immunological propeties as those of the HIV-2 viruses deposited with the CNCM under n°s I-502 or I-532. The definitions of criteria of equivalence will be returned to later.

The invention also relates to a method for producing the HIV-2 virus or variants of the latter in permanent cell lines derived from T4 lymphocytes, or lymphocytes bearing the T4 phenotype, this method consisting in culturing these lines which have been infected beforehand with HIV-2 virus and, in particular when the level of reverse transcriptase activity has reached a specified threshold, in recovering the amounts of virus released into the culture medium.

A preferred permanent line for the purpose of culturing HIV-2 is, for example, of the HUT 78 cell type. An HUT 78 line infected with HIV-2 was deposited on 6th Feb. 1986 with the CNCM under n° I-519. Culturing is, for example, carried out as follows:

The HUT 78 cells (10$^6$/ml) are co-cultured with infected normal human lymphocyte (10$^6$/ml). The culture medium is RPMI 1640 with 10%. foetal calf serum. After 15 to 21 days, a cytopathogenic effect is observed in the HUT 78 cells. The reverse transcriptase is assayed one week after this observation, in the culture supernatant. It is then possible to begin to recover the virus from this supernatant.

Another preferred line for culturing belongs to the lines known under the designation CEM.

The infection and then the culturing of the infected CEM cells can be carried out, in particular, as follows.

T4 lymphocytes infected beforehand with HIV-2 virus and uninfected cells of the CEM line are co-cultured for the time required for infection of the CEM. The culture conditions are then, moreover, continued in a suitable medium, for example that described below, and when the reverse transcriptase activity of the infected cells has reached a sufficient level the virus produced is recovered from the culture medium.

In particular, co-culturing was carried out, under the conditions specified below, of human T4 lymphocytes. which had been infected five days beforehand with a strain of HIV-2 virus originating from a patient hereinafter designated "ROD", on the one hand, and CEM, on the other hand.

The infected T4 lymphocytes, activated beforehand with phytohaemagglutinin, proved to possess a reverse transcriptase activity of 5.000 cpm/10$^6$ normal T lymphocytes three days after the beginning of the infection. Culturing was continued until the measured reverse transcriptase activity reached 100.000 cpm in the supernatant. These T4 lymphocytes were then placed in contact with CEM cells (3×10$^6$ infected normal T lymphocytes) and reincubated in the following culture medium: RPMI 1640 containing 2.92 mg/ml of L-glutamine, 10% of decomplemented foetal calf serum, 2 ug/ml of Polybrene, 0.05% of anti-interferon-alpha serum, 100.000 ug/ml of penicillin, 10 ug/ml of streptomycin and 10.000 ug/ml of neomycin.

The culture medium is changed twice weekly.

The measurements of reverse transcriptase activity measured in the supernatant were as follows:

| | |
|---|---|
| on day 0: | 1.000 (background) |
| on day 15: | 20.000 |
| on day 21: | 200.000 |
| on day 35: | 1.000.000 |

A CEM culture infected with HIV-2 virus was deposited with the Collection Nationale de Cultures de Microorganismes (CNCM) of the Institut Pasteur under n° I-537 on 24th Mar. 1986.

A few characteristics of the antigens and nucleic acids involved in the structure of HIV-2 emerge from the experiments carried out under the conditions described below. They will, in many cases, be better assessed by comparison with the same type of characteristics relating to other types of retrovirus, in particular HIV-1 and SIV.

In that which follows, reference will be made to the drawings, in which:

FIGS. 1*a*, 1*b* and 1*c* relate to crossed immunoprecipitation experiments between sera, respectively, of patients infected with HIV-1 and HIV-2, and of rhesus monkeys infected with STLV-III, on the one hand, and viral extracts of HIV-1, on the other hand;

FIGS. 2*a* and 2*b* show comparative results for the electrophoretic mobilities of the proteins of HIV-1, HIV-2 and STLV-III respectively, in SDS-polyacrylamide gels;

FIG. 6 is a nucleotide sequence of a portion of E2, this sequence corresponding to the U3/R region of HIV-2;

Figures 7A, 7B:
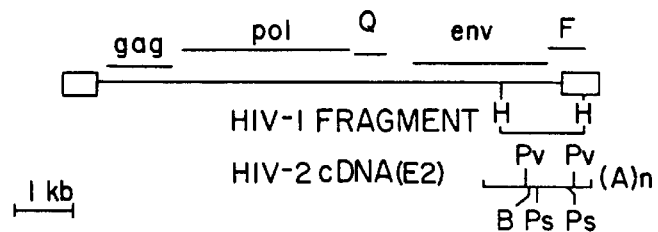
Figure 8A:
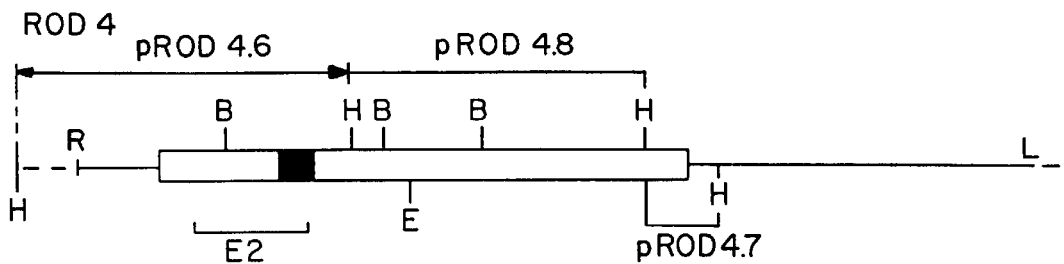
Figure 8B:
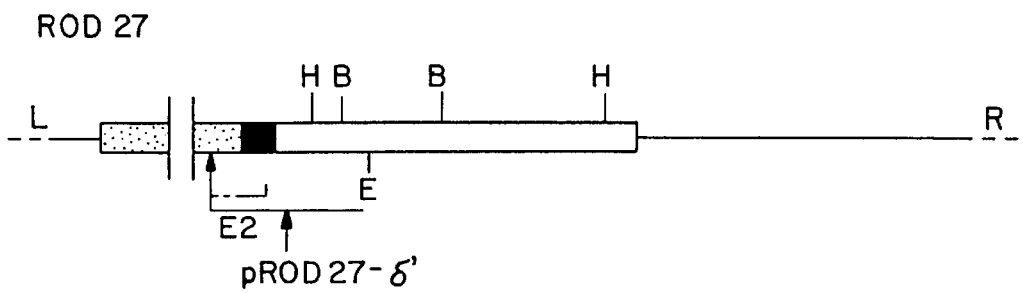
Figure 8C:
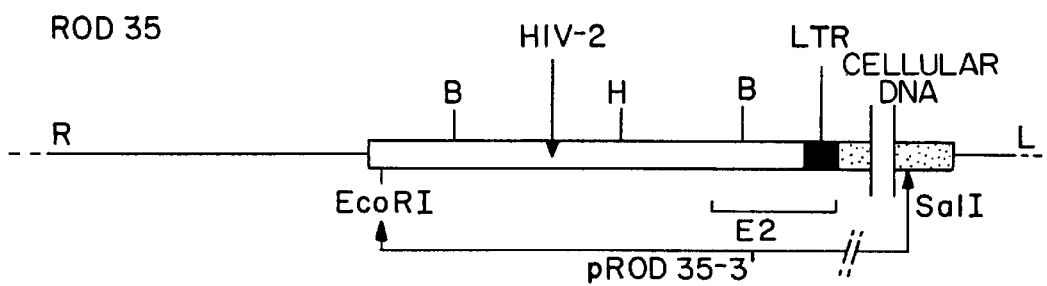
Figure 9:
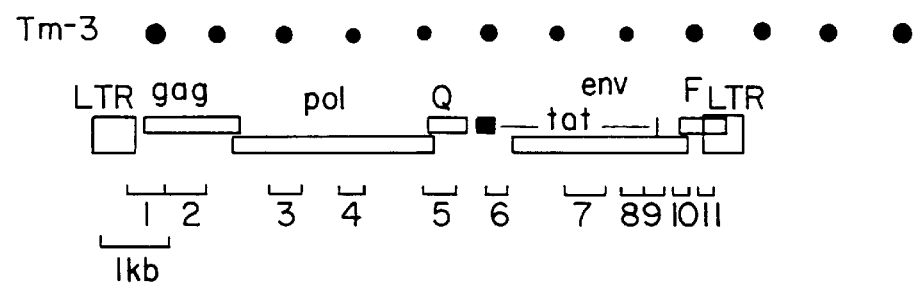

FIG. 7 shows:
  on the one hand, and schematically, structural elements of HIV-1 (FIG. 7A) and, aligned with a region containing the HIV-1 3' LTR, the sequence derived from the E2 region of the HIV-2 cDNA, and
  on the other hand, the common nucleotides present, respectively, in the sequence derived from the E2 region of HIV-2 and in the corresponding sequence of HIV-1 placed in alignment at the cost of a number of deletions and insertions (FIG. 7B);

FIG. 8 shows schematically the structures of several clones of a phage modified by several inserts originating from the cDNA derived from HIV-2 (clones ROD4, ROD27 and ROD35); sequences derived, in their turn, from ROD4, ROD27 and ROD35, subcloned in a plasmid pUC18, have also been shown schemetically in this figure, these latter sequences being placed to correspond with the regions of ROD4, ROD27 and ROD35 from which they respectively originate;

FIG. 9 shows the relative intensities of hybridization between
  a/ eleven fragments removed from different regions of the complete HIV-1 genome (the fragments being shown schematically at the bottom of the figure), on the one hand, and the HIV-2 cDNA, present in ROD4, on the other hand, and
  b/ fragments originating from HIV-2 with the same cDNA.

Generelly, the HIV-2 antigens used in the comparative tests, the description of which follows, originate from the HIV-2 MIR strain deposited with the CNCM under n° I-502, and the DNA sequences derived from the genomic DNA of HIV-2 originate from the strain HIV-2 ROD deposited with the CNCM under n° I-352.

I—ANTIGENS, IN PARTICULAR PROTEINS AND GLYCOPROTEINS

The virus initially cultured in HUT 78 was labelled metabolically with [$^{35}$S]systeine and [$^{35}$S]methionine, the infected cells being incubated in the presence of these radioactive amino acids in culture medium devoid of the corresponding unlabelled amino acid, for a period of 14 to 16 hours, especially according to the technique described in the paper designated as reference (21) in the bibliography presented at the end of the description, as regards the labelling with [$^{35}$S]cysteine. The supernatant is then clarified and the virus then ultracentrifuged for one hour at 100.000 g on a cushion of 20% sucrose. The principal antigens of the virus separated by electrophoresis in a polyacrylamide gel (12.5%) under denaturing conditions (SDS), or in a gel composed of poly-acrylamide (10%)+ bisacrylamide (0.13%) with SDS (0.1% final concentration). The following coloured markers are used as molecular weight references:

| | |
|---|---|
| myosin: | 200 kd |
| phosphorylase B: | 97.4 kd |
| BSA: | 68 kd |
| ovalbumin: | 43 kd |
| α-chymotrypsin: | 25.7 kd |
| β-lactoglobulin: | 18.4 kd |
| lysozyme: | 14.3 kd |

Other molecular weight markers were used in other experiments. This applies, in particular, to FIGS. 1a, 1b and 1c, which refer to other known molecular weight markers (under the letter M in these figures). The Antigens are still more readily distinguished after immuno-precipitation (RIPA) or by immunoimprinting (Western blot), using the antibodies present in the patient's serum: their apparent molecular weights, determined by their apparent migrations, are very close to those of the HIV-1 antigens.

It is generally specified that, in the text which follows, the numbers which follow the designations "p" and/or "gp" correspond to the approximate molecular weights of the corresponding proteins and/or glycoproteins, divided by 1000. For example, p36 has a molecular weight of the order of 36.000. It is, however, understood that these molecular weight values can vary within a range which can reach 5%, 10% or even more, depending on the techniques used for the determination of these molecular weights.

Repetition of the experiments enabled the apparent molecular weights of the HIV-2 antigens to be determined more accurately. Thus, it was found that the molecular weights of the three core proteins, which had initially been assigned molecular weights of the order of 13.000, 18.000 and 25.000, respectively, in fact had apparent molecular weights closer to the following values: 12.000, 16.000 and 26.000, respectively. These proteins are hereinafter designated by the abbreviations p12, p16 and p26.

The same considerations apply to the existence of protein or glycoprotein bands whose apparent molecular weights were assessed at values which could range from 32.000 to 42.000–45.000. Repetition of the measurements finally enabled a band corresponding to an apparent molecular weight of 36.000 to be precisely defined. In the text which follows, this band is designated by the abbreviation p36. Another band at 42.000–45.000 (p42) is consistently observed also. One or other of p36 or p42 probably constitutes a transmembrane glycoprotein of the virus.

A major envelope glycoprotein having a molecular weight of the order of 130–140 kd is consistently observed: this glycoprotein is designated hereinafter by the term gp140.

It is appropriate to note that, in general, the molecular weights are assessed with an accuracy of ±5%, this accuracy even being capable of becoming a little lower for antigens of high molecular weight, as was fournd for gp140 (molecular weight of 140±10%). This group of antigens (when they are labelled with [$^{35}$S]cysteine is only faintly recognized, if at all, by sera of patients containing anti-HIV-1 antibodies in the detection systems used in the laboratory or by the use of tests employing HIV-1 lysates, such as those marketed by DIAGNOSTICS PASTEUR under the name "ELAVIA". Only the p26 protein was weakly immunoprecipitated by such sera. The envelope protein was not precipitated. The serum of the patient infected with the new virus (HIV-2) faintly recognizes a p34 protein of HIV-1. In the detection system used, the other HIV-1 proteins were not recognized.

In contrast, HIV-2 possesses some proteins which show some immunological relationship with comparable structural proteins or glycoproteins, separated under similar conditions from a retrovirus recently isolated from captive macaques of the rhesus species, whereas this immunological relationship tends to become obliterated, for other proteins or glycoproteins. This latter retrovirus, which is presumed to be the aetiological agent of AIDS in monkeys, was designated by the investigators who isolated it [bibliographic references (16–18) below] by the name "STLV-III$_{mac}$". For convenience of reference, it will be designated in the text which follows simply by the term "STLV-III" (or alternatively by the term SIV, an abbreviation for "Simian Immunodeficiency Virus").

Another retrovirus, designated "STLV-III$_{AGM}$" or SIV$_{AGM}$), has been isolated in wild green monkeys. However, in contrast to the virus present in rhesus monkeys, the presence of "STLV-III$_{AGM}$" does not appear to induce an AIDS-type disease in African green monkeys.

Nevertheless, the immunological relationship of the structural proteins and glycoproteins of HIV-2 on the one hand and the STLV-III $_{mac}$ and STLV-III$_{AGM}$ retroviruses on the other hand, and consequently the relationship of their nucleic acid sequences, remains limited. Experiments have enabled a first distinction to be established between the retroviruses capable of infecting man or monkeys; the following emerges;

The HIV-2 virus does not multiply in chronic fashion in the lymphocytes of rhesus monkeys when it has been injected in vivo and under working conditions which permit the development of the STLV-III$_{mac}$ virus, as have been described by N. L. Letvin et al., Science (1985), vol. 230, 71–75.

This apparent inability of HIV-2 to develop in monkeys under natural conditions enables the HIV-2 virus, on the one hand, and the STLV-III virus isolates, on the other hand, to be differentiated biologically.

Employing the same techniques as those recorded above, it was found that it was also possible to obtain the following from STLV-III a principal p27 core protein, having a molecular weight of the order of 27 kilodaltons, a major envelope glycoprotein, gp140, a p32 protein, probably transmembrane, which is not observed in RIPA when the virus has been labelled beforehand with [$^{35}$S]cysteine, but which can be observed in immuno-imprinting experiments (Western blots) in the form of broad bands.

The major envelope glycoprotein of HIV-2 has proved to be immunologically closer to the major envelope glycoprotein of STLV-III than to the major envelope glyco-protein of HIV-1.

These findings apply not only in respect of the molecular weights, 130–140 kilodaltons for the major glycoproteins of HIV-2 and STLV-III compared with approximately 110 for the major envelope glycoprotein of HIV-1, but also in respect of the immunological properties, since sera drawn from patients infected with HIV-2, and more especially antibodies formed against the HIV-2 gp140, recognize the STLV-III gp140 whereas, in comparable experiments, the same sera and the same antibodies to HIV-2 do not recognize the HIV-1 gp110. However, anti-hiv-2 do not recognize the HIV-1 gp110. However, an-ti-HIV-1 sera which have never reacted with the HIV-2 gp140s precipitate a [$^{35}$S]cysteine-labelled 26 kd protein present in extracts of HIV-2.

The major core protein of HIV-2 appears to have an average molecular weight (approximately 26.000) intermediate between that of the HIV-1 p25 and the p27 of STLV-III.

These observations are derived from experiments carried out with viral extracts obtained from HIV-2 isolated from one of the abovementioned patients. Similar results have been obtained with viral extracts of HIV-2 isolated from the second patient.

Cells infected, respectively, with HIV-1, HIV-2 and STLV-III were incubated in a medium containing 200 μCi/ml of [$^{35}$S]cysteine in a medium free from unlabelled cysteine for 16 hours. The clarified supernatants were centrifuged at 60.000 g for 90 minutes. The pellets were lysed in an RIPA buffer (1), immunoprecipitated with different sera and then subjected to electrophoresis on polyacrylamide gel charged with sodium dodecyl sulphate (SDS-PAGE).

Figure 1A:
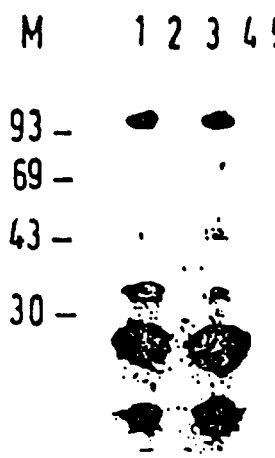
Figure 1B:
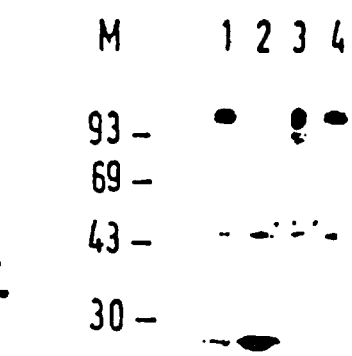
Figure 1C:
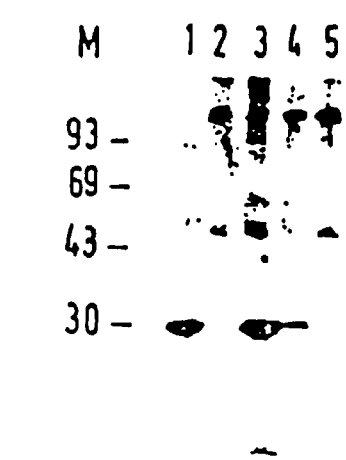

The results observed are illustrated by FIGS. 1a, 1b and 1c.

FIG. 1a shows the observed results of immunoprecipitation between a viral extract of HIV-1 obtained from a CEM C1.13 cell line and the following sera, respectively:

anti-HIV-1-positive serum (band 1), serum obtained from the first patient mentioned above (band 2), serum of a healthy African carrier of anti-HIV-1 antibodies (band 3), serum obtained from a macaque infected with STLV-III (band 4), and serum of the second patient mentioned above (band 5).

In FIG. 1b, there are recorded the observed results of immunoprecipitation between the HIV-2 antigens obtained from the first patient, after prior culture with HUT-78 cells, and different sera, more especially the serum of the abovementioned first patient (band 1), the anti-HIV-1-positive serum (band 2), the serum of the macaque infected with STLV-III (band 3) and the serum of the abovementioned second patient (band 4).

Finally, FIG. 1c illustrates the observed results of immunoprecipitation between the antigens of an STLV-III isolate obtained from a macaque having a simian AIDS. The sera used, to which the bands 1 to 5 refer, are the same as those recorded above in relation to FIG. 1a.

M refers to the markers myosin (200 kd), galactosidase (130 kd), bovine serum albumin (69 kd), phosphorylase B (93 kd), ovalbumin (46 kd) and carbonic anhydrase (30 kd).

Figure 2A:
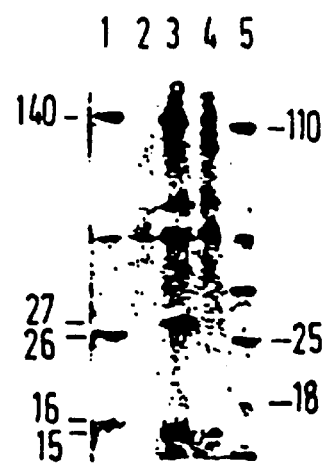
Figure 2B:
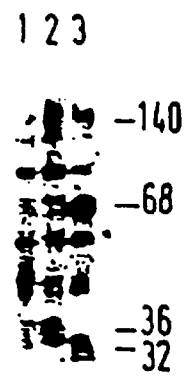

FIGS. 2a and 2b show comparative results for the electrophoretic mobilities of the proteins of HIV-1, HIV-2 and STLV-III.

FIG. 2a relates to the experiments carried out with extracts of virus labelled with [$^{35}$S]cysteine, after immunoprecipitation on SDS-PAGE. The different bands relate to the following virus extracts: virus obtained from patient 1 and irmmunoprecipitated by the serum originating from the same patient (band 1), extract of the same virus immunoprecipitated with a negative control serum originating from a person not carrying anti-HIV-1 or anti-HIV-2 antibodies (band2), extxact of STLV-III virus immunoprecipitated with a serum originating from a macaque infected with STLV-III (band 3), immunoprecipitation observed between extracts of the same virus and a negative control serum (band 4), and extract of HIV-1 immunoprecipitated with the serum of a European patient infected with AIDS.

FIG 1b shows the results obtained in Western blot (immuno-imprinting) experiments. Cell lysates originating from uninfected or infected HUT-78 cells were subjected to electrophoresis on SDS-PAGE, and then transferred electrophoretically to a nitrocellulose filter before being reacted with the serum of the abovementioned first patient (serum diluted ¹⁄₁₀₀). The nitrooellulose filter was then washed and the detection of the bound antibodies visualized with $^{125}$I-labelled goat anti-human IgG.

The spots observed in bands 1, 2 and 3 relate, respectively, to the agglutination experiments between the abovementioned serum and extracts of uninfected HUT-78 cells (band 1), extracts of HUT-78 cells infected with an HIV-2 virus (band 2) and extracts of HUT-78 cells infected with STLV-III (band 3). The numbers which appear in the margins beside each of the bands correspond to the approximate molecular weights of the most representative viral proteins (molecular weights in kilodaltons).

II—NUCLEIC ACIDS

1/ The RNAs of the HIV-2 retrovirus

The RNA of the virus, deposited on a filter according to the "spot blot" technique, did not hybridize, under stringent conditions, with the DNA of HIV-1.

By "stringent conditions", there are understood the conditions under which the hybridization reaction between the RNA of the HIV-2 and the chosen probe, radioactively labelled with $^{32}$p (or labelled in a different manner), followed by the washing of the probe, are carried out. The hybridization, on a membrane, is carried out at 42° C. in the presence of an aqueous solution particularly of 50% formamide (volume/volume) in 0.1% SDS/5×SSC for 18 hours. The membrane on which the hybridization reaction has been carried out is then washed at 65° C. in a buffer containing 0.15% of SDS and 0.1×SSC.

By "non-stringent conditions", there are understood the conditions under which the hybridization reaction and the washing are carried out. The hybridization is carried out by bringing into contact with the chosen probe, labelled with $^{32}$p (or otherwise labelled), namely at 42° C. in a 5×SSC buffer, 0.1% SDS, containing 30% of formamide for 18 hours. The washing of the membrane is carried -out at 50° C. with a buffer containing 01% of SDS and 2×SSC.

Hybridization experiments were also carried out with a hybridization probe consisting of a recombinant plasmid pBT1 obtained by cloning the DNA of HIV-1 originating from λJ19 (Cell 1985, vol. 40, p. 9) in the vector pUC18. Under non-stringent conditions, only very weak hybridization was observed between the RNA of HIV-2 and the cloned DNA derived from HIV-1.

Other probes containing cloned sequences of HIV-1 were used: p1 a/ single-stranded probes of subgenomic DNA of HIV-1, produced from subclones of the HIV-1 genome and inserted in phage M13. The cloned regions related to the protease gene or the "endonuclease" gene.

Only one probe of the endonuclease region of HIV-1 (nucleotide sequence between bases n°s. 3760 and 4130) gave a weak hybridization under non-stringent conditions with HIV-2. The "protease" probe (HIV-1 nucleotide sequence between bases n°s. 1680 and 1804) did not hybridize even under non-stringent conditions with HIV-2.

b/ A probe pRS3, consisting of the sequence coding for the "envelope" region of HIV-1 (subcloning in pUC18) did not give hybridization under non-stringent conditions with HIV-2.

The "spot blot" technique is also known as "dot blot" (transfer by spots).

Figure 3:
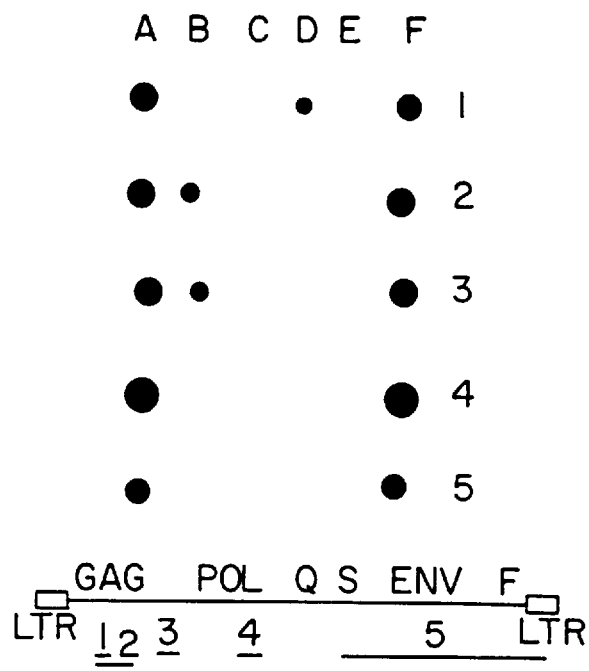
FIG. 3 shows the results oL crossed hybridization between genomic sequences of HIV-1, HIV-2 and STLV-III on the one hand, and probes containing different subgenomic sequences of the HIV-1 virus, on the other hand.

Further results of hybridization between genomic RNAs of HIV-1, HIV-2 and STLV-III, on the one hand, and probes containing different subgenomic sequences of the HIV-1 virus, on the other hand, appear in FIG. 3.

The supernatants of the different culture media (in the proportion of 0.5 to 1 ml for each spot) were centrifuged for 5 minutes at 45.000 revolutions per minute; the pellets were resuspended in an NTE buffer containing 0.1% of SDS and deposited on a nitrocellulose filter. The latter was pre-soaked in a 2×SSC medium (0.3M NaCl, 0.03M sodium citrate). After baking (for 2 hours at 80° C.), the filters were hybridized with various probes contraining genomic subfragments of HIV-1, under non-stringent conditions (30% formamide, 5×SSC, 40° C.), washed at 50° C. with a 2×SSC solution containing 0.1% of SDS and then autoradiographed for 48 hours at −70° C. with enhancing screen.

The probes 1–4 are single-stranded probes obtained by the "prime cut" method as described in (25). Briefly, the single-stranded fragments originating from the M13 virus and bearing subgenomic HIV-1 inserts (30) were ligated to oligomeric fragments (17 nucleotides) originating from M13 (BIOLABS). The complementary strand was then synthesized with Klenow enzyme in a TM buffer (10 mM Tris, pH 7.5, 10 mMMgCl$_2$) in the presence of dATP, dGTP, dTTP and dCTB, labelled with $^{32}$p at the alpha-position (Amersham, 3000 Ci/mmol). The DNA was then digested with the appropriate restriction enzymes, heat denatured and subjected to electrophoresis on a denaturing polyacrylamide gel (containing 6%. of acrylamide, 8M urea in a TDE buffer). The gel was then autoradiographed for 5 minutes. The probe was then cut out and eluted in a 300 mM NaCl, 0.1% SDS buffer. Specific activities (SA) of these single-stranded probes were estimated at $5\times10^8$–$10^9$ disintegrations per minute/microgram (dpm/ug).

The characteristic sequence present in the different probes were as follows:

Probe 1: nucleotides 990–1070,

Probe 2: nucleotides 980–1260,

Probe 3: nucleotides 2170–2240

Probe 4: nucleotides 3370–3640.

The numbering of the above nucleotides are those envisaged in the paper under reference (30).

Lastly, the probe 5 consists of a plasmid pUC18 bearing the EcoR1-Sac1 fragment of the HIV clone in λj19 (31), which was subjected to nick translation to obtain an SA of approximately $10^8$ dpm/μg.

The relative arrangements of the subgenomic fragments present in the probes with respect to the whole HIV-1 genome are shown schematically in FIG. 3. The different spots correspond, respectively, as follows:

spot A: a virus is obtained from a culture of CEM C1.13 cells infected with HIV-1, spot B : a virus is obtained from HUT-78 cells infected with STLV-III, spots C and D: isolates obtained, respectively, from the viruses of the abovementioned two African patients, spot E: negative control cell extract obtained from uninfected HUT-78 cells, spot F: virus obtained from a patient from Zaïre suffering from AIDS, which had been cultured in normal T lymphocytes in the presence of TCGF.

All the spots were obtained with an amount of virus corresponding to 25.000 dpm of reverse transcriptase activity, except for the spots C: 15.000 dpm.

The following observations were made :

The genomic. RNAs of the two HIV-2 isolates obtained from purified viral particles did not hybridize with any of the probes under the stringent conditions described above, although the viral particles were isolated and purified from culture supernatants of highly infected cells showing evidence of high reverse transcriptase activity.

Under the non-stringent conditions described above, the following observations were made: all the probes hybridized intensely with the genomic RNAs obtained from the control HIV-1 preparations and from another isolate obtained from a patient from Zaïre suffering from AIDS.

Two of the probes obtained (nucleotides 990–1070 and 990–1260, both originating from the gag region of HIV-1) hybridized slightly with the spots from extracts of the HIV-2 retroviruses; only one of these two probes (nucleotides 990–1260) also showed slight hybridization with the STLV-III spot (FIG. 3). As regards the probe containing a fragment of the pol region (nucleotides 2170–2240), hybridization was observed with STLV-III and, albeit much more weakly, with the RNA of HIV-2. The other probe of the pol region (nucleotides 3370–3640) did not give hybridization with any of the HIV-2 and STLV-III spots.

Lastly, the probe modified by nick translation and containing the entire env gene and the LTR (nucleotides 5290–9130) of HIV-2 did not hybridize either with the RNAs of STLV-III or with those of HIV-2.

It will also be noted that anoter probe which contained the 5' end of the Pol reading frame of HIV-1 (corresponding to the protease region) did not hybridize either with the RNAs of HIV-2 or with the RNAs of STLV-III.

It consequently also results from the foregoing that the HIV-2 virus appears more remote, from the structural standpoint, from the HIV-1 virus than it is from STLV-III. HIV-2 nevertheless differs significantly from STLV-III, which bears out the different results observed in respect of the infective capacities of the HIV-2 viruses, which are virtually nil in monkeys, compared with the unquestionable ineffective capacities of STLV-III viruses in these same specites of monkeys.

The restriction maps and the genomic RNA sequences of HIV-2, or of the cDNAs obtained from these genomic RNAs are accessible to those versed in the art, since the strains of HIV-2 deposited with the CNCM can, after suitable multiplication, provide him with the genetic equipment required for the determination of these restriction maps and nucleotide sequences. The conditions under which the restriction map of the genome of one of the HIV-2 isolates of this invention were established, and the conditions under which certain portions of cDNA derived from these genomes were sequenced, are described below.

Figure 4:
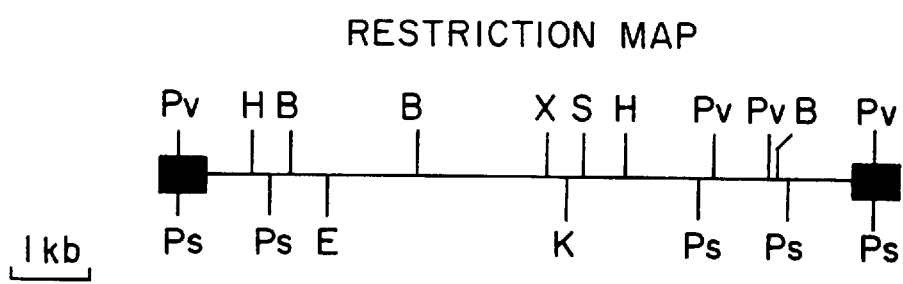
FIG. 4 is a restriction map of the cDNA derived from the RNA of HIV-2 ROD.
Figure 5:
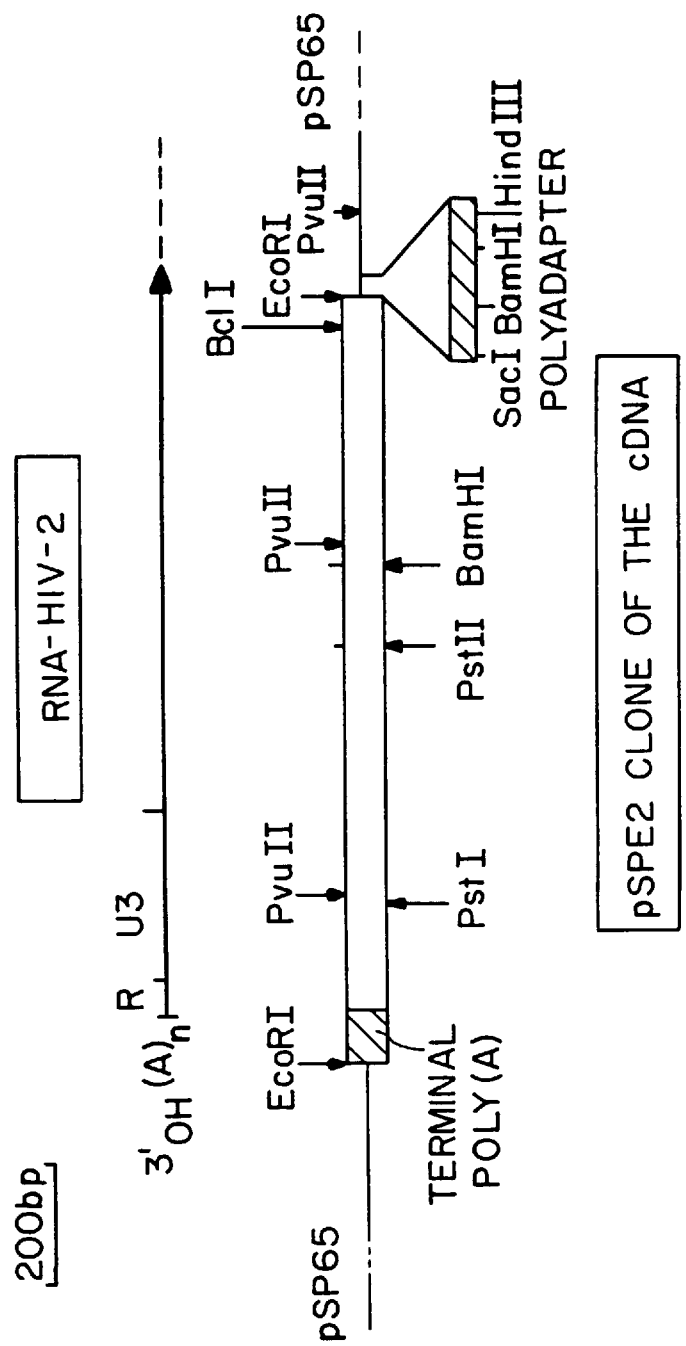
FIG. 5 is a restriction map of an E2 fragment of the cDNA derived from HIV-2, this fragment containing a region corresponding to the 3' LTR region of HIV-2.

The restriction map of the genome of a retrovirus which is representative of HIV-2 retroviruses is shown in FIG. 4. The restriction map of a substantial fragment of this cDNA is shown in FIG. 5. Finally, a portion of this latter fragment has been sequenced.

This sequence, and a number of the restriction sites which it contains, are shown in FIG. 6. The cloned whole cDNA— or cloned fragments of this cDNA—can themselves be used as specific hybridization probes.

2/ cDNA and fragments of this cDNA derives, respectively, from the RNA of HIV-2

The conditions under which the abovementioned cDNA was obtained are described below.

The first stage of manufacture of this cDNA comprised the production of an oligo(dT) serving as a primer or of an initiator cDNA strand, by carrying out an endogenous reaction activated by a detergent, using the reverse transcriptase of HIV-2, on purified virions obtained from supernatants of infected CEM cells. The CEM cell line was a lymphoblastoid CD4+cell line described by G. E. Foley et al. in Cancer 18: 522–529 (1965), which is considered to be incorporated herein by reference. These CEM cells used are infected with an ROD isolate, which was shown to produce substantial amounts of HIV-2 continuously.

After the synthesis of the second strand (in the presence of nucleotides and a bacterial DNA polymerase), the double-stranded cDNAs were inserted into a bacterial phage vector M13 TG130. A phage library of $10^4$ recombinant M13 phages was obtained and subjected to an in situ screening with an HIV-1 probe. The latter contains a 1.5 kb fragment originating from the 3' end of the cDNA derived from the RNA of the LAV isolate (shown in FIG. 7A). Approximately 50 positive plaques were detected, purified and characterized by crossed hybridization of the inserts and sequencing of the ends.

This procedure enabled different clones to be isolated, containing sequences approximately complementary to the 3' end of the polyadenylated RNA of the LTR [abbreviation for "long terminal repeat" of HIV-1, described by S. Wain Hobson et al. in Cell 40: 9–17 (1985)] region, considered to be incorporated herein by reference.

The largest of the inserts of the group of M13 clones in question, which hybridize with the 3' LTR region of HIV-1, is an approximately 2 kb clone designated E2. Like the 3' LTR region of HIV-1, the clone E2 contains an AATAAA signal situated approximately 20 nucleotides upstream from a poly(A) terminal portion, and a 3' LTR region corresponding to that of HIV-2. After partial sequencing, this 3' LTR region of HIV-2 proved to possess a distant relationship with the homologous region of HIV-1.

FIG. 5 is a restriction map of the fragment of E2 (elongated rectangular area) incorporated in plasmid pSPE2 which contains it. It comprises part of the R region and the U3 region of HIV-2. The drawing does not show the boundaries of the R and U3 regions.

The sequence of part of E2 is shown in FIG. 6. The positions of specific restriction sites are indicated therein. The small degree of relationship between the 3' LTR regions of HIV-1 and HIV 2 is illustrated in FIG. 7. In effect, only approximately 50% of the nucleotides of the two LTR sequences can be placed in alignment (approximately 50% sequence homology), at the cost of some insertions or deletions. In comparison, the sequence homology of the corresponding regions of the different variant American and African isolates of HIV-1 is greater than 95%, without insertion or deletion.

The clone E2 was used as a specific probe for HIV-2, for the identification on a hybridization filter of the sequences originating from HIV-2 and present in other clones.

This probe also detects the genomic RNA of HIV-2 under stringent conditions. It likewise permits detection, by the so-called "Southern blot" method on the DNA of CEM or similar cells infected with an ROD isolate or with other HIV-2 isolates. No signal is detected under the same stringency conditions in tests of hybridization of this probe with cDNAs originating from uninfected cells or from cells infected with HIV-1.

These results confirmed the exogenous nature of HIV-2 with respect to HIV-1. An approximately 10 kb species, probably corresponding to the non-integrated viral DNA, was detected as a principal constituent in the undigested DNA of cells infected with HIV-2. Anoter DNA having an apparent size of 6 kb, possibly corresponding to a circular form of the viral DNA, was also detected.

The other portions of the HIV-2 genome were also identified. For this purpose, a genome library was constructed in phage lambda L47. Phage lambda L47.1 has been described by W. A. M. Loenen et al. in Gene 10 249–259 (1980), which publication is considered to be incorporated herein by reference.

The genome library is constructed with fragments obtained by digestin of the DNA originating from the CEM cell line infected with HIV-2 ROD, after digestion with the enzyme Sau3AI.

Approximately 2×10⁶ recombinant plaques were screened in situ with a clone containing the labelled E2 insert of the HIV-2 cDNA. Ten recombinant phages were detected on plaques and purified. The restriction maps of three of these phages, characterized by their capacity for "Southern blot" hybridization with the E2 insert under stringent conditions, as well as with subgenomic probes of HIV-1 under non-stringent conditions.

A clone bearing a 9.5 kb insert and derived from the whole circular viral DNA, containing the complete HIV-2 genome, was identified. It was designated "Lambda ROD 4". The other two clones, Lambda ROD 27 and Lambda ROD 35, derived from integrated proviruses, bear LTR sequences of the viral coding sequences and adjacent cell DNA sequences. The different sequences are shown in FIG. 8.

Fragments of the Lambda clones were subcloned in plasmid vector pUC18. The fragments originating from λ ROD 4, λ ROD 27 and λ ROD 35, and subclones respectively, in the abovementioned plasmid vector, are also seen in FIG. 8. The following sublclones were obtained:

pROD 27-5, derived from Lambda ROD 27, contains a 5.2 kb region of the HIV-2 genome and adjacent cell sequences (5' LTR and 5' coding viral sequence around an EcoRI site);

pROD 4.8, derived from Lambda ROD 4, contains an approximately 5 kb HindIII fragment. This fragment corresponds to the central portion of the HIV-2 genome;

pROD 27-5' and pROD 4.8 contain HIV-2 inserts chich overlap each other;

pROD 4.7 contains a 1.8 kb HindIII fragment of Lambda ROD 4; this fragment is placed in the 3 direction with respect to the subcloned fragment in pROD 4.8, and contains approximately 0.8 kb of coding viral sequences and a portion situated between the BamHI and HindIII cloning sites of the left arm of phage Lambda (Lambda L 47.1);

pROD 35 contains all the HIV-2 coding sequences in the 3 direction with respect to the EcoRI site, the 3' LTR end and approximately 4 kb of adjacent nucleotide sequences of cellular origin;

pROD 27-5' and pROD 35, present in E. coli HB were deposited on Nov. 21, 1986 with the CNCM under 1-626 and I-633;

pROD 4.7 and pROD 8, present in E. coli TG1, were deposited on Nov. 21, 1986 with the CNCM, respectively, under n°s I-627 and I-628.

The complete HIV-2 ROD genome, the restriction map of which is seen in FIG. 4, was reconstituted from pROD 35, linearized beforehand with EcoRI, and pROD 27-5'. The EcoRI insert of pROD27-5 was ligated in the correct orientation in the EcoRI site of pROD 35.

The degree of relationship between HIV-2and the other human or simian retroviruses was assessed by mutual hybridization experiments. The relative homology between the different regions of HIV-1 and HIV-2 genomes was determined by tests of hybridization of fragments originating, respectively, from cloned HIV-1 genome and from radioactively labelled lambda ROD 4. The relative positions of these fragments (numbered from 1 to 11) with respect to the HIV-1 genome are seen at the bottom of FIG. 9.

Even under very low stringency conditions (Tm-42° C.), the HIV-1 and HIV-2 genomes hybridize only at the level of their respective gag genes (spots 1 and 2), reverse transcriptase regions in pol (spot 3), end regions of pol, Q (or sor) genes (spot 5) and F (or 3' orf) genes and 3' LTR (spot 11). The HIV-1 fragment used for detecting the first cDNA clones of HIV-2 corresponds to the subclone of spot 11, which hybridizes relatively well with HIV-2 under non-stringent conditions. A signal originating from spot 5 is the only one which persists after stringent washing. The envelope gene, the tat gene region and part of pol appear to be highly divergent. These data, as well as the sequence obtained with LTR (FIG. 3), demonstrate that HIV-2 is not (at all events, as regards its envelope) a variant of HIV-1.

It is observed that HIV-2 is more closely relate to SIV [described by M. D. Daniel et al in Science 228:1201–1204 (1985)], which must be considered to be incorporated herein by reference] than it is to HIV-1.

All the proteins of SIV, including the envelope protein, are immunoprecipitated by sera of patients infected with HIV-2, while the serological cross-reactivity of HIV-1 and HIV-2 is limited to the core proteins. However, SIV and HIV-2 can be distinguished by the differences mentioned above in respect of the molecular weights of their proteins.

As regards the nucleotide sequences, it is also noted that HIV-2 is related to SIV.

Furthermore, the characterization of HIV-2 also makes it possible to demarcate the region of the envelope glycoprotein which is responsible for the binding of the virus to the surface of the target cells and the subsequent internalization of the virus. The interaction takes place via the CD4 molecule itself, and it appears that HIV-1 and HIV-2 use the same receptor. Thus, although there are large differences between the env genes of HIV-1 and 2, the restricted homologous regions of the envelopes of the two forms of HIV can be considered to be constituents of binding to a common receptor of T4 lyphocytes. These sites are called on to form epitopes bearing the immunogenicity of peptides which might be used to elicit in man a protective immunoresponse against HIV viruses.

Advantageous sequences for forming probes in hybridization reactions with the genetic material of patients carrying viruses or proviruses, in particular for detecting the presence of HIV-2 virus RNA in their lymphocytes, contain a nucleotide sequence resulting from the combination of 5 kb HindIII fragments of ROD 4 and E2 cDNA. The experiments can be carried out by all methods, in particular by the "Northern blot", "Southern blot" and "dot blot" techniques.

Further characteristics of the invention will also emerge, without implied limitation, in the course of the description which follows of examples of identification of certain portions of the retroviral genome and of the production of a number of recombinant DNAs involving various portions of a cDNA derived from the retroviral genome of HIV-2.

EXAMPLES

Example I

DNA probe, for use in kits for diagnosis of HIV-2

A cDNA complementary to the genome RNA, obtained from purified virions, was prepared by the following method:

The supernatant obtained after 48 hours' culturing of CEM cells infected with an HIV-2 ROD isolate of HIV-2 was ultracentrifuged. The centrifugation pellet containing the virion was centrifuged on a sucrose gradient to form a new centrifugation pellet, substantially by the same method as that described in European Patent Application 84/401.234-0.138.667, already mentioned.

The purified HIV-2 preparation was used for the synthesis of cDNA, employing an endogenous reaction activated by a detergent.

In summary, the virion preparation was added to a reaction mixture containing 50 mM Tris-HCL, 5 mM MgCl$_2$, 10 mM DTT, 0.025% of the detergent marketed under the name TRITON, and 50 μM of each of the 4 deoxynucleoside triphosphates and an oligo(dT) initiator. The reaction was carried out for 90 minutes at 37° C.

After extraction with phenol of the proteins present in the first reaction medium, the second cDNA chain was synthesized in the presence of RNAse, *E. coli* DNA polymerase 1 and the 4 deoxynucleotides, for 1 hour at 15° C. and 1 hour at 22° C. Blunt ends were created on this double-stranded cDNA by the action of T4 DNA polymerase. All the reagents for this procedure are commercially available (AMERSHAM cDNA kit) and were used as recommended by the supplier.

After (1) ligation of adapters (linkers) containing an EcoRI site (marketed by Pharmacia) to the blunt ends of the cDNA in the presence of a T4 DNA ligase (marketed by BIOLABS), (2), digestion of these linkers with the restriction endonuclease EcoRI, and (3) removal of the linker fragments by gel filtration (gel column marketed under the name ULTROGEL) on AcA 34 (LKB-IBF), the cDNA is inserted in an M 13 TG 130 vector cleaved with EcoRI. A library of cDNAs was obtained after transformation of *E. coli* strain TG1. Approximately $10^4$ recombinant M13plaques were obtained.

To select, in the cDNA library, recombinant M13 clones containing the HIV-2 cDNA, the technique of plaque hybridization was used. The DNA of the M13 plaques was transferred to nitrocellulose filters and hybridized with subgenomic HIV-1 probes derived from the "lambda J19" clone of an LAV (or HIV) virus decribed in the European patent application. This probe contained an insert consisting of a portion having an approximate length of 1500 base pairs (bp) of HIV-1 DNA. This insert was bounded by two HindIII restriction sites, respectively, inside the open reading frame of the "env" gene and in the R segment of the 3' LTR end of HIV-1. This probe contained the 3' end of the env gene, the whole F gene, the U3 segment and a portion of the R segment of the LTR, having an approximate length of 1500 base pairs (bp).

The probe containing the 1.5 kg HindIII insert was labelled with [$^{32}$P]-dCTP and -dTTP (3000 Ci×10$^{-3}$ mole) by incubating the probe in the presence of initiators and Klenow DNA polymerase I for 4 hours at 15° C. (using an AMERSHAM kit). The tests of hybridization of the cDNA clones of the library were performed overnight under low stringency conditions, in a solution of a hybridization medium containing 5×SSC, 5×Denhart, 25% of formamide, 100 μg/ml of denatured salmon sperm DNA and the labelled probe (2×10$^7$ cpm with a specificity of 10$^9$ cpm/μg) at 37° C. The filters were subjected to three washing stages, successively in the presence of the three solutions whose compositions are stated as follows:

Washing n° 1: 5×SSC, 0.1% SDS, at 25° C. for 4×15 minutes

Washing n° 2: 2×SSC, 0.1% SDS, at 42° C. for 2×30 minutes

Washing n° 3: 0.1×SSC, 0.1%SDS, at 65° C. for 2×30 minutes

Each washing is followed by autoradiography of the filters.

Several positive clones were detected after washing n° 1 and were still detected after washing n°2. However, all the signals disappeared after washing n° 3. This indicates that the positive clones had only a weak relationship with the HIV-1 genome, which was nevertheless sufficient to perform the abovementioned selection. The positive clones were subcultured, redeposited on plaques and again hybridized with the same probe under the stringency conditions corresponding to washing n° 1. Most of them were still positive.

The clones were also selected using a total human DNA probe under conditions of moderate stringency and by hybridization in 5×SSC, 5×Denhart and 40% formamide, followed by washing in 1×SSC, 0.1% SDS at 50° C. None of the previously positive clones was detected, and consequently did not correspond to specific repeated DNA or to the cDNA of the ribosomal RNA.

The positive M13 recombinant clones were cultured in a liquid medium and characterized as follows:

(1) Size of their insertion

An M13 single-stranded type DNA was obtained from each individual clone, and the synthesis of the second strand was performed with an M13 17-mer initiator sequence and the Klenow enzyme. The inserts were excised using EcoRI (BOEHRINGER) and analysed by agarose gel electrophoresis. The majority of the inserts contained from 200 to 600 and 200 bp, with the exception of the clone designated E2.1, which had an approximate length of 2 kbp.

(2) Analysis of the nucleotide sequence

Several clones were partially sequenced using the dideoxy method of Sanger et al., described in Proc. Natl. Acad. Sci. 74:5463–7 (1977) which forms part of the present description. Various independent clones contained similar nucleotide sequences, with the exception of the poly(A) chains at their 3' ends, the lengths of which were different. These results demonstrate that these cDNA clones were derived from the RNA template. Detailed sequence analysis of these cDNA clones, including the 3' end of the HIV-2 genome, showed a limited relationship with HIV-1.

(3) Hybridization with the genomic RNA and DNA of HIV-2

(a) Production of the genomic RNA of HIV-2:

An infected supernatant was centrifuged (50.000 revolutions, 30 minutes). The pellet of the deposit was resuspended in 10 mM Tris pH 7.5, 1 mM EDTA, 0.1% SDS. One of the insertion clones, F1.1, was labelled and used as a probe for hybridization with the genomic RNA of different viral isolates, according to the "dot-blot" technique.

The "dot-blot" technique comprised the following stages:

(i) Depositing the sample (HIV-2 lysate) in spots on a nitrocellulose membrane soaked beforehand in 20×SSC (3M NaCl, 0.3M sodium citrate) and dried in the air, (ii) baking the membrane for 2 hours at 80 C., and (iii) performing the hybridization.

This hybridization was performed under high stringency conditions (5×SSC, 5×Denhart, 50% formamide at 42° C.). It was followed by washing in 0.1×SSC, 0.1% SDS at 65° C. Under these conditions, the probe hybridizes strongly to the spots originating from two independent isolates of HIV-2, including LAV-II ROD, from which the cloned cDNA originated. A weak hybridization signal was detected with the spot formed by STLV-III mac [Simian T-lymphotropic Virus (also known as "SIV"), type III macaque], and no hybridization was detected with the HIV-1 isolates.

The "Southern blot" experiments, employing the clone E2.1 containing the 2 kb insert as a $^{32}$p-labelled probe, did not reveal any hybridization with the DNAs of uninfected cells, but detected bands iii detached cells infected with HIV-2, under high stringency conditions. HIV-2 shows polymorphism at levels of its restriction map which are equivalent to those of the restriction maps of HIV-1. With the complete cellular DNA of infected cells, two types of signal are detected by the "Southern blot" method:. (1) in DNA fractions having molecular weights MW of approximately 20 kb and more, in the case of integrated forms of the virus, and (2) in the fractions of Lower MW (9,10 kb) in the case of the virus not integrated in the genome.

These characteristics are highly specific to a retrovirus.

Some experiments performed with STLV-III (SIV-3) from infected cells enabled it to be established that the simian retrovirus is relatively distant from HIV-2 (the signal is detected exclusively under low stringency conditions). These experiments show that the abovementioned probes permit the specific detection of HIV-2.

(4) Subcloning of the cDNA of HIV-2 in a bacterial plasmid vector

The positive M13 clone, E 2.1, was selected and subcloned in a plasmid vector. The DNA of the recombinant M 13 (TG 130) phage E 2 was purified in the form of a single-stranded DNA (M-13-ROD-E2) containing the 2 kb insert containing the 3' portion of the HIV-2 genome (obtained from HIV-2 ROD). This insert was transferred to plasmid pSP65, described by Melton, D. A., in 357 Nucleic Acid Res. 12:035–7056 (1984).

A second chain was constructed in vitro in the presence of the 17-mer initiator sequence (AMERSHAM), the four nucleotides A, C, T, G, and DNA polymerase I (Klenow). The EcoRI insert was excised by EcoRI digestion and purified on agarose gel, and then ligated to pSP65 which had itself been digested beforehand with EcoRI. The ligation mixture was used to transform $E.coli$ strain DH1, and recombinants were selected on the basis of their capacity for resistance to ampicillin. The recombinants identified were cultured on LB medium (Luria medium) containing 50 $\mu$g/ml of ampilillin. These recombinant plasmids were purified and monitored for the presence of the correct inserted fragment.

One of the clones obtained, designated by the reference pSPE2, was deposited with the CNCM in Paris, France, under access $n^o$ I-595 on 5th Sep. 1986.

The inserts derived from the cDNAs of HIV-2 and which were present inserted in the abovementioned probe contained the nucleotide sequence which has been defined above, in conformity with a part of E2.

Example II

Cloning of a cDNA complementary to the DNA complementary to the genomic RNA of HIV-2 virions HIV-2 virions were purified from 5 litres of a culture supernatant from a CEM line infected with a ROD isolate. A first strand of cDNA was synthesized in contact with sedimented purified virus, in the presence of an oligo(dT) initiator and employing an endogenous reaction activated by a detergent, according to the technique described by Alizon et al., Nature 312, 757–760 (1984). The RNA/cDNA hybrids were purified by extraction with a phenol/chloroform mixture and by precipitation with ethanol. The second strand of cDNA was produced in the presence of DNA polymerase I/RNAse H, according to the method described by Gubler and Hoffman ( ). The description in this paper is considered to be incorporated herein by reference.

The double-stranded cDNA was provided with blunt ends in the presence of DNA polymerase T4, using the constituents of a cDNA synthesis kit marketed by AMERSHAM.

EcoRI adaptors (linker), marketed by PHARMACIA were attached to the end of the cDNA; the cDNA thereby modified was inserted, after digestion in the presence of EcoRI, into a dephosphorylated phage vector M13tg130 which was itself digested with EcoRI, also marketed by AMERSHAM. A cDNA band was obtained after transformation of $E.coli$ strain TG1. Recombinant plaques ($10^4$) were screened in situ on filters permitting replicas by hybridization with the clone J19 containing the 1.5 kb HindIII fragment mentioned above, originating from HIV-1.

The filters were prehybridized in the presence of a medium containing 5×SSC, 5×DENHARDT solution, 25% formaldehyde and denatured salmon sperm DNA (100 micro-grammes/ml), at 37° C. for 4 hours, and then hybridized for 16 hours in the same buffer (Tm-42° C) in the presence of additional labelled probe (4×10 cpm), to provide a final hybridization buffer solution containing $10^6$ cpm/ml.

Washing was carried out with a 5×SSC, 0.1% SDS solution at 25° C. for 2 hours (it being understood that 20×SSC corresponds to a 3M NaCl and 0.3M sodium citrate solution). The plaques which responded positively were purified and the M13 single-stranded DNAs were prepared and their ends sequenced according to the method of Sanger et al.

Hybridization of a DNA of cells infected with HIV-1 and HIV-2 and of RNAs of HIV-1, HIV-2 and of SIV virions, respectively, with a probe derived from a cloned cDNA of HIV-2

The DNAs were extracted from infected CEM cells continuously producing HIV-1 and HIV-2, respectively. DNA samples of these two retroviruses, digested in some cases with 20 $\mu$g of PstI, and undigested in other cases, were subjected to electrophoresis on 0.8% agarose gel and transferred by the "Southern" method to a nylon membrane. Small volumes of infected supernatant, taken up in an NTE buffer containing 0.1. of SDS and having the same reverse transcriptase activity, were deposited on nitrocellulose which had been soaked beforehand in a 2×SSC solution.

A prehybridization was carried out in a solution containing 50% of formamide, 5×SSC, 5×Denhart and 100 mg/ml of denatured salmon sperm DNA, for 4 hours at. 42° C. A hybridization was performed in the same buffer, to which 10% of dextran sulphate and $10^6$ cpm/ml of E2 labelled insert (specific activity $10^9$ cpm/$\mu$g) had been added, for 16 hours at 42° C. Two washings were then carried out with a 0.1×SSC, 0.1% SDS solution for 30 min each. After exposure for 16 hours to an intensifying screen, the Southern spot is dehybridized in 0.4N NaOH, neutralized, and rehybridized under the same conditions with the HIV-1 probe labelled with $10^9$ cpm/$\mu$g.

Example III

Cloning in phage lambda of the complete DNA of the HIV-2 provirus

The DNA of CEM cells infected with HIV-2 ROD (FIG. 2, bands a and c) is partially digested with Sau3AI. The 9–15 kb fraction was selected on a 5–40% sucrose gradient and ligated to the BamHI arm of the lambda L47.1 vector. The plaques ($2\times10^6$) obtained after in vitro packaging and deposition on $E.coli$ strain LA 101 were screened in situu by hybridization with the insert of the E2 cloned cDNA. Approximately 10 positive clones were purified on plaques and propagated in $E.coli$ C600 recBC. The clones lambda ROD 4, ROD 27 and ROD 35 were amplified, and their DNAs characterized by drawing up their restriction maps and by hybridization by Southern's method with the cDNA clone of HIV-2 under stringent conditions and with the gag-pol probes of HIV-1 under non-stringent conditions.

FIG. 8 shows schematically the structures of 3 of the recombinant phages obtained, ROD 4, ROD 27 and ROD 35.

The elongated rectangular portions of these diagrams correspond to proviral sequences originating from the DNAs of the initially infected CEM cells, the clear portions corresponding to retroviral sequences, the shaded portions to portions of cellular DNAs and the black portions to the LTR in the said viral sequences.

The thin lines designated by the letters L and R correspond to the arms originating from the Lambda L47.1 phage vector which was used for the cloning.

Some of the restriction sites have also been indicated: these are, more especially, the following sites: B: BamHI; E: EcoRI; H: HindIII; K: KpnI; Ps: PstI; Pv: PvuII; S: SacI; X: XbaI.

These viral sequences have portions in common with the E2 sequence. The relative positions of these portions, determined by hybridization with E2, are also seen in the figures.

ROD 4 is derived from a circular viral DNA. ROD 27 and ROD 35 are derived from proviruses integrated in a cellular DNA structure.

Lastly, the inserts subcloned under the conditions described above, and their relative positions with respect to the corresponding ROD 4, ROD 27 and ROD 35 sequences, are shown in these figures.

These are, more especially, the inserts of plasmids pROD 27-5', pROD 35-3', pROD 4.6, pROD 4.8 and pROD 4.7.

FIG. 9 is a representation of the relative intensities of the hybridization spots which were produced between ROD-4 and sub-fragments 1 to 11 originating, respectively, from the different portions of a single-stranded DNA originating from an M13 subclone containing a nucleic acid derived from the whole LAV genome. The relative positions of these various fragments with respect to the whole LAV genome (determined by sequencing) are shown at the bottom of the figure. Point 12 corresponds to a control spot produced using a control DNA of the phage lambda.

The hybridization experiments in the spot transfer (dot blot) method were carried out under the low stringency conditions of Example II using, by way of a probe, the lambda ROD 4 recombinant containing the total cDNA of HIV-2. The washings were then carried out successively under the following conditions: 2×SSC, 0.1% SDS at 25° C. (Tm-42° C.), 1×SSC, 0.1% SDS at 60° C. (Tm-20° C.) and 0.1%×SSC, 0.1% SDS at 60° C. (Tm-3° C.).

The spots shown were obtained after radiographic exposure overnight.

Example IV
In vitro diagnostic test for the presence of HIV-2 virus in a biological medium MATERIAL AND METHODS
Patients HIV-2-infected patients were recruited among individuals visiting the Egas Moniz Hospital in Lisbon either for hospitalization or for consultation, between September 1985 and September 1986. For this selection, all individuals of African origin or having stayed in Africa underwent a serum, test for antibodies against both HIV-1 (Immunofluorescence -IFA- and/or ELISA) and HIV-2 (IFA). Only those patients who were proved serologically to be infected with HIV-2 were included in the study.

Virus isolation

In 12 patients, HIV isolation was attempted as previously described. Briefly, the patients' peripheral blood lymphocytes (PBL) were stimulated with PHA, co-cultured with normal human PHA-stimulated PBLs and maintained in the presence of interleukin-2 (IL-2). Cultures were monitored for the presence of cytopathic effect (CPE) and for reverse transcriptase (RT) activity in the supernatant.

Immunofluorescence assay (IFA)

IFA slides were prepared as follows: HIV-2-infected MOLT-4 cells were washed twice in PBS and layered onto IFA glass slides ($10^4$ cells/well), air dried and fixed with cold acetone. For IFA these cells were reacted with a 1/10 dilution of the test serum for 45 minutes at 37° C., washed, dried, and reacted with a fluorescein-conjugated goat antihuman IgG, A, M (1/100 diluted) for 30 minutes at 37° C. After washing, cells were counterstained in 0.006% Evans blue, mounted in 90% glycerol, 10% PBS and examined under a fluorescence microscope.

ELISA

Some patients' sera were examined for antibodies to HIV-1 using the commercially available serum tests ELAVIA (Pasteur Diagnostics) or ABBOTT.

Radioimmunoprecipitation assay (RIPA)

HIV-1 or HIV-2 infected CEM cells were cultured in the presence of $35_S$ cysteine (200 micioCi/ml) for 16 hours. The supernatant was collected, viral particles were pelleted and lysed in RIFA buffer (Tris-HCL 50 mM pH 7.5, NaCl 150 mM, EDTA 1 mM, 1% Triton ×100, sodium deoxycholate 0.1%, SDS 0.1%). For each reaction, 50 microliters of a dilution of lysate corresponding to $10^5$ cpm was reacted with 5 microliters of test serum for 18 hours at 4° C. Immune complexes were bound to Sepharose-protein A (PHARMACIA), washed, and eluted by boiling for 2 minutes. Eluted antigens were then analysed by SDS-polyacrylamide gel electrophoresis and autoradiography.

Dot-blot hybridization

Virus isolated from patients' PBLs were pelleted and lysed in Tris-HCL 10 mM pH 7.5, NaCl 10 mM, EDTA 1 mM, SDS 0.5%. One microliter of each lysate, corresponding to 50.000 cpm of RT activity, was deposited onto nitro-cellulose. Hybridization and washing were conducted in high stringency conditions: hybridization in 6×SSC, 5×Denhart, 50% formamide, for 18 hours at 42° C.; and washing in 0.1×SSC, 0.1% SDS at 65° C. W, used HIV-1 and HIV-2 probes, $^{32}P$ labeled to a specific activity of $10^8$ cpm/microgram. The HIV-1 probe corresponds to the complete genome of the $LAV_{BRU}$ isolate, and HIV-2 probe was derived from a 2 kilobases cDNA clone from $LAV-2_{ROD}$ isolate.

RESULTS
Patient population

Thirty patients with serological and/or virologic evidence of HIV-2 infection were studied. They were 12 males and 18 females. The mean age was 35, ranging 11–55. All patients, except one, have stayed for several years in West Africa: 26 were born and living in Guinea-Bissau and 2 were originating from the Cape Verde Islands. One patient wan an 11-year old boy from Angola who had lived in the Cape Verde islands for several years. The only European in the study population was a 40 year-old Portuguese man who had lived for 8 years in Zaïre, and denied any stay in West Africa.

Clinical Presentation

Among the 30 patients 17 had AIDS, according to the CDC criteria. The major symptom in these patients was chronic diarrhoea, together in most cases with a weight loss of more than 10 kilograms in a year. In 10 patients the diarrhoea was found to be associated with the presence of an intestinal opportunistic infection; in 7 cases the pathogen was Isospora belli alone, one patient had Cryptosporidium alone and 2 had both pathogens. In 3 cases no opportunistic intestinal pathogen was found. Among all 17 AIDS cases, oesophageal candidiasis was diagnosed in 8. Six AIDS patients had respiratory symptoms. Pulmonary tuberculosis was diagnosesφ in 2 and another unidentified mycobacterium was found in one. Two patients had pulmonary aspergillosis, one following a tuberculosis. Two other AIDS patients had recurrent episodes of pneumonitis with no pathogen identified and one patient had Pneumocystis carinii pneumonia, which was only diagnosed post-mortem. Four of the 17 AIDS patients had Kaposi's sarcoma: in 3 cases it appeared limited to the skin, and in one patient post-mortem examination revealed disseminated visceral lesions. Central nervous system disorders were found in 2 AIDS patients: one had cerebral lymphoma, and the other had subacute encephalitis of unknown cause.

Four patients were presenting with the symptoms of the AIDS-related complex (ARC): two had diffuse lymphadenopathy with persistent fever, one had chronic diarrhoea with weight loss, and one had recurrent episodes of bronchopneumonia and multiple lymphadenopathies.

Among the 9 remaining patients, 6 had no symptoms that could be considered as related to HIV infection, one had pulmonary tuberculosis alone, one had persistent diffuse lymphadenopathy alone, and one presented with neurologic syphillis. During the 12 months' period of the study 7 patients died, all presenting with AIDS.

Serological studies

Each patient had at least one serum test for antibodies to both HIV-1 and HIV-2. All patients' sera were tested by IFA for antibodies to HIV-2, and all were positive. Among them, 21 were also tested for antibodies to HIV-2 by RIPA: all clearly precipitated the high-molecular weight envelope glycoprotein of the virus, termed gp 140, and 16 of them also reacted with the major core protein p26, whereas only one reacted with another viral core protein, termed p16.

The sera were evaluated for the presence of cross-reacting antibodies to HIV-1 using different assays. An IFA test was used in 24 sera: 12 were negative, 10 were weakly reactive, and 2 were positive. In ELISA, 21 were tested: 16 were negative, and 5 were positive. Finally, 11 sera were tested for antibodies to HIV-1 proteins by RIPA. Three failed to react with any viral protein, 2 only precipitated the pol gene product p34, and 5 reacted with the major core protein p25. Two sera reacted only faintly with the envelope glycoprotein gp 110 of HIV-1. These two sera, and all sera with positive IFA or ELISA tests for antibodies to HIV-1, had a strong reactivity with the gp 140 of HIV-2 in RIPA, indicative of infection with HIV-2 rather than with HIV-1. Only one patient, that we did not include in the study population, was serologically found to be infected with HIV-1 and not with HIV-2. This patient was a 21-year-old woman from Central Africa (Sao Tome Islands) with AIDS.

Virus isolation

Isolation of retroviruses from peripheral blood lymphocytes was attempted in 12 patients. HIV was isolated in 11, according to the presence of a typical cytopathic effect, and of a peak of particle-associated reverse transcriptase activity in the culture supernatants.

All 11 isolates were identified as HIV-2 using a dot-blot hybridization technique. Viral dots from 10 isolates were found to strongly hybridize in stringent conditions of hybridization and washing with a HIV-2 probe derived from a cloned HIV-2 cDNA, whereas none of them hybridized with a HIV-1 probe in the same conditions. One isolate only faintly hybridized with the HIV-2 probe, but it failed to hybridize with the HIV-1 probe.

Immunological evaluation

Thirteen patients were evaluated for the number of circulating lymphocytes identified as helper T cells (CD4+) and the ratio of helper:supressor T cells. Among these patients, 11 had AIDS: their mean absolute helper T cells count was 243+300/microliter and their mean helper: suppressor ratio was 0.25+0.15. One patient, clinically presenting with ARC, had a number of helper T lymphocytes of 240/microliter and a ratio of 0.18. Another patient, with neurological syphillis and no evident HIV-related symptom, had a helper T lymphocyte count of 690/microliter and a ratio of 0.82.

DISCUSSION

In this study, we demonstrated HIV-2 infection in 30 West African patients presenting either with AIDS, ARC or with no apparent HIV-related symptoms. The results nevertheless permit the conclussion that HIV-2 must be considered to be a major aetiological agent of AIDS in West African patients. The serological and virologic profiles that we observed indicate that HIV-2 infection was not often associated with HIV-1 infection in our patients. Despite important antigenic and genetic differences, HIV-1 and HIV-2 display similar tropism for CD4+ T lymphocytes, similar cytopathic effects, similar morphology, and share common immunoreactive epitopes in some of their constitutive proteins. Since all West African patients with HIV infection in this study were found to be infected with HIV-2 and none of them with HIV-1, the new virus HIV-2 may be the major cause of AIDS in West Africa.

The symptoms of HIV-2-related AIDS were not different from those of HIV-1 related AIDS in Central Africa: The most common symptom was chronic diarrhoea, with important weight loss, mostly due to Isospora belli and/or Cryptosporidium. The frequency of other opportunistic infections, such as candidiasis, mycobacteria (including M. tuberculosis) and toxoplasmosis was found comparable to that in HIV-1-related African AIDS. Pneumocystis carinil pneumonia, a very common complication of AIDS in the USA and Europe, has only been found once in our study, and cryptococcal meningitis was not detected.

Nevertheless, the immunological abnormalities found in HIV-2-infected AIDS patients are identical to those described in HIV-1-related AIDS.

Among the 30 patients, who all had serum antibodies reactive with HIV-2 antigens, only 7 had HIV-1 specific antibodies detectable using IFA or ELISA. In RIPA, all of these 7 patients had antibodies reactive with the other major core proteins p25 (HIV-1) or p26 (HIV-2), which share strongly immunoreactive epitopes. Five patients lacked such antibodies: all 5 had a negative HIV-1 ELISA. IFA was borderline in 3 and negative in 2. However, although some of them were not completely evaluated, we found 9 patients with serum antibodies to the viral core protein p26 of HIV-2 who had a weakly reactive or negative HIV-1-specific IFA and/or ELISA. These findings point to the importance of including HIV-2 antigens in the HIV Serum tests used in Africa and perhaps in other areas.

A retrovirus was isolated from the peripheral lymphocytes of 11 patients. In all cases, viral growth was obtained within 2 weeks, characterized by the presence of reverse transcriptase activity in the culture supernatant and of cytopathic effect. However, this cytopathic effect appeared to vary in importance from one isolate to another: some isolates provided numerous large sized syncytia together with important cell lysis, whereas others exhibited only few syncytia of limited size, and affected poorly the viability of the culture.

RNA from all but one isolate was found to clearly hybridize in high stringency conditions with a prove derived from a HIV-2 cDNA clone, representing the 3' end of the genome. None hybridized with a HIV-1 prove in the same conditions. This demonstrates that the isolates infecting these patients all belonged to the same type of virus. One isolate only poorly hybridized with HIV-1. This virus, however, was isolated from a patient with serum antibodies reacting with all the antigens of HIV-2 in RIPA.

This invention relates generally, in addition to HIV-2 virus its variants, to any equivalent virus which is infectious for man and possesses immunological characteristics specific to HIV-2. The invention relates generally to any virus which, in addition to the properties possessed by the HIV-2 viruses deposited with the CNCM, also possesses the characteristics which follow.

The preferred target for the HIV-2 retrovirus consists of human Leu 3 cells (or T4 lymphocytes) and and "immortalized" cells derived from these T4 lymphocytes, for example cells of the HUT 78 lines dealt with in the context of this patent application. In other words, it has a specific tropism for these cells. It can be cultured in permanent lines of the HUT, CEM, MOLT or similar type, expressing the T4 protein. It is not infectious for T8 lymphocytes. It is cytotoxic for the human T4 lymphocytes. The cytopathogenic nature of HIV-2 viruses with respect to T4 lymphocytes manifests itself, in particular, by the appearance of multinucleated cells. It has a reverse transcriptase activity which requires the presence of $Mg^{2+}$ ions and has a strong affinity for polyadenylate oligodeoxythymidylate (poly(A)-oligo (dT) 12–18). It has a density of approximately 1.16 in a sucrose gradient. It has a mean diameter of 140 nanometers and a core having a mean diameter of 41 nanometers. The lysates of the virus contain a p26 protein which does not cross immunologically with the p24 protein of HTLV-1 virus or HTLV-II virus. These p26 proteins hence have a molecular weight which is slightly higher (by approximately 1000) than the corresponding p25 proteins of HIV-1 and slightly lower (again, of the order of approximately 1000 lower) than the corresponding p27 proteins of the SIV. The lysates of HIV-2 contain, in addition, a p16 protein which is not immunologically recognized by the p19 protein of HTLV-1 or of HTLV-II in RIPA (abbreviation for radioimmunoprecipitation assay) experiments. They contain, in addition, an envelope glycoprotein having a molecular weight of the order of 130,000–140,000, which does not cross immunologically with the gp 110 of HIV-1 but which, on the other hand, crosses immunologically with the gp 140 envelope glyco-protein of STLV-III. These lysates also contain proteins or glycoproteins which can be labelled with ($^{35}$S) cysteine, having molecular weights, respectively, of the order of 36,000 and 42,000–45,000. The genomic RNA of HIV-2 does not hybridize with the genomic RNA of HIV-1 under stringent conditions. Under non-stringent condition, it does not hybridize with nucleotide sequence derived from HIV-1 and containing the env gene and the LTR adjacent to it. In particular, it does not hybridize with the nucleotide sequence 5290–9130 of HIV-1, nor with sequences of the pol region of the HIV-1 genome, in particular with the nucleotide sequence 2170–2240. Under non-stringent conditions, it hybridizes weakly with nucleotide sequences of the HIV-1 region, in particular the nucleotide sequences 990–1070 and 990–1260.

It should be noted that any retrovirus which is infectious for man, capable of inducing one of the forms of AIDS, having the abovementioned essential properties and whose genomic RNA is capable of hibridizing under stringent conditions with those HIV-2 viral strains deposited with the CNCM (or with a cDNA or cDNA fragment derived from these genomic RNAs is to be considered to be an equivalent of HIV-2.

The invention also relates to each of the antigens, in particular proteins and glycoproteins in the purified state, such as may be obtained from HIV-2. Reference to "purified" proteins or glycoproteins implies that these proteins or glycoproteins lead, respectively, only to single bands in polyacrylamide gel electrophoresis, in particular under the experimental conditions which have been described above. Any suitable method of separation and/or purification for obtaining each of these can be used. By way of example of a technique which can be employed, that describes by R. C. MONTELARO et al., J. of Virology, June 1982, pp. 1029–1038, will be mentioned.

The invention relates generally to all antigens, in particular proteins, glycoproteins or polypeptides, originating from an HIV-2 and having immunological properties equivalent to those of these antigenic compounds of HIV-2. Two antigens are said to be "equivalent", in the context of this account, inasmuch as they are recognized by the same antibodies, in particular antibodies which can be isolated from a serum obtained from a patient who has been infected with an HIV-2, or inasmuch as they meet the conditions for "immunological equivalence" stated below.

Among equivalent polypeptides, proteins or glycoproteins, there must be included fragments of the above antigens (or peptides reconstituted by chemical synthesis), inasmuch as they give rise to immunological cross-reactions with the antigens from which they are derived. In other words, the invention relates to any polypeptide which has, in common with abovementioned antigens, identical or similar epitopes capable of being recognized by the same antibodies. Belonging to this latter type of polypeptides are the products of expression of corresponding sequences of the DNAs which code for the corresponding polypeptide sequences.

The HIV-2 virus has proved to be usable as a source of antigens for detecting antibodies in all people who have come into contact with the HIV-2 virus.

The invention relates generally to any composition which can be used for the diagnosis of the presence in a biological fluid serum, in particular of people who have come into contact with HIV-2, of antibodies against at least one of the antigens of HIV-2. This composition can be applied to the selective diagnosis of the corresponding variety of AIDS, employing diagnostic techniques such as those described in the European patent application cited above, except that lysates or purified antigens of HIV-2 are used instead of those of HIV-1. In this connection, the invention relates more especially to compositions containing at least one of the proteins p12, p16, p26, which are the internal proteins, or p36 or gp 140. By way of examples of compositions, those which simultaneously contain the following will be mentioned.

p26 and gp 36 p26, p36 and gp 140, p12, p16 and p26, p16, p26 and gp 140, etc.

it is self-evident that these compositions signify only examples. In particular, the invention relates to the viral extracts or lysates containing this group of proteins and/or glycoproteins or all fractions from which one or more of the abovementioned proteins or glycoproteins has been separated beforehand.

The invention also relates to compositions containing a combination of proteins and/or glycoproteins of an HIV-2 with proteins and/or glycoproteins of an HIV-1, for example:

either core proteins of HIV-1 and HIV-2, in particular the p25 of an HIV-1 and p26 of an HIV-2, or alternatively the p18 of an HIV-1 and the p16 of an HIV-2, or envelope glycoproteins of an HIV-1 and envelope glycoproteins of an HIV-2, in particular the gp 110 of HIV-1 and the gp 140 of HIV-2, or alternatively the p42 of HIV-1 and the p36 or p42–45 of HIV-2, or, of course, mixtures of proteins and/or glycoproteins of an HIV-1 and proteins and/or glycoproteins of and HIV-2.

Such compositions, used for diagnosis, consequently make possible procedures for diagnosis of AIDS or of the symptoms which are associated with it, which extend over a wider spectrum of the aetiological agents responsible. It goes without saying that the use for diagnostic procedures of compositions which contain only proteins and/or glycoproteins of HIV-2 is nevertheless useful for more selective diagnosis of the category of retrovirus which can be held responsible for the disease.

The invention also relates to the DNAs or DNA fragments, pore especially cloned DNAs and DNA fragments, obtained from the RNA and cDNAs derived from the RNA of the HIV-2 retrovirus. The invention also relates especially to all equivalent DNAs, in particular any DNA possessing sequence homologies with the DNA of HIV-2, especially with the sequences which code for the env and pol regions of the strain of HIV-2 deposited with the CNCM, equal at least to 50%, preferably to 70% and still more advantageously to 90%. It will also be stated generally that the invention relates to any equivalent DNA (or RNA) capable of hybridizing with the DNA or RNA of HIV-2 in the "spot blot" technique, under non stringent conditions as defined above.

The invention likewise relates to the sera capable of being produced in animals by inoculating the latter with HIV-2. The invention hence relates more especially to the polyclonal antibodies directed more specifically against each of the antigens, in particular proteins or glycoproteins, of the virus. It also relates to the monoclonal antibodies which can be produced by traditional techniques, these monoclonal antibodies being directed, respectively, more specifically against the different proteins of HIV-2.

These polyclonal or monoclonal antibodies can be used in different applications. Their use for neutralizing the corresponding proteins, or even inhibiting the infectivity of the whole virus, will mainly be mentioned. They can also be used, for example, for demonstrating the viral antigens in biological preparations or for carrying out procedures for purification of the corresponding proteins and/or glycoproteins, for example by using them in affinity chromatography columns.

It is understood that, in general, the available technical literature (in particular that for which the bibliographic references are in the context of the present description) in respect of HIV-1 and the virus designated HTLV-III is to be considered to be incorporated herein by reference, inasmuch as the techniques described in this literature are applied under similar conditions to the isolation of HIV-2 virus or of the equivalent viruses, and to the production from these viruses of their different constituents (in particular proteins, glycoproteins, polypeptides and nucleid acids). Use can also be made of the teachings of this technical literature as regards the application of the different constituents in question, in particular to diagnostic procedures of the corresponding forms of LAS or AIDS.

The present invention relates more especially to a method for in vitro diagnosis of AIDS, which comprises bringing a serum or another biological medium originating from a patient who is the subject of the diagnosis into contact with a composition containing at least one of the proteins or glycoproteins of HIV-2, or alternatively an extract or lysate of the virus, and the detection of the immunological reaction. Examples of such compositions have been stated above.

Preferred methods involve, for example, immunoenzymatic reactions of the ELISA or immunofluorescence type. The titrations can be measurements by direct or indirect immunoflueorescence, by direct or indirect immunoenzymatic assays.

Thus, the present invention also relates to extracts of virus (either an extract of one or more HIV-2 viruses alone, or a mixture of extracts originating from one or more HIV-2 viruses, on the one hand, and one or more HIV-1 viruses, on the other hand), these extracts being labelled. Any suitable type of label can be used: enzymatic, fluorescent, radioactive and the like.

Such titrations comprise, for example:

the deposition of specified amounts of the extract or of the composition referred to according to the present invention in the wells of a microtitration plate;

introduction into these wells of increasing dilution of serum principally containing the antibodies whose presence is to be detected in vitro;

the incubation of the microtitration plate;

careful washing of the microtitration plate with a suitable buffer;

the introduction into the wells of the microtitration plate of labelled antibodies specific for human immunoglobulins, the labelling being carried out with an enzyme chosen from those which are capable of hydrolysing a substrate in such a way that the latter then undergoes a modification of its absorption of radiation, at least in particular wavelength band, and the detection, preferably in comparative fashion relative to a control, of the extent of hydrolysis of the substrate, as a measurement of the potential risks or of the effective presence of the disease.

The present invention also relates to outfits or kits for the above diagnosis, which comprise:

an extract or a more highly purified fraction of the types of virus stated above, this extract or fraction being labelled, for example radioactively, enzymatically or by immunofluorescence;

anti-(human immunoglobulins) or a protein A (advantageously, bound to a support which is insoluble in water, such as agarose beads);

an extract of lymphocytes obtained from a person in good health;

buffers and, where appropriate, substrates for the visualization of the labelling.

It emerges from the foregoing that the invention relates to the diagnosis of HIV-2 virus, or of a variant, as a result of the use of the probes described above, in a method employing different stages recorded below, these stages being arranged specifically to bring out the characteristic properties of the HIV-2 virus.

The invention naturally also relates to the use of the cDNAs or their fragments (or reombinants containing them) as probes for the diagnosis of the presence or absence of HIV-2 virus in samples of serum or of other biological fluids or tissues obtained from patients suspected of being carriers of the HIV-2 virus. These probes are preferably also labelled (radioactive, enzymatic, fluorescent labels, and the like). Especially advantageous probes for carrying out the method for diagnosis of the HIV-2 virus, or of a variant of HIV-2, can be characterized in that they comprise all or a fraction of the cDNA complementary to the genome of the HIV-2 virus, or alternatively, in particular, the fragments present in the various clones identified above. There will be mentioned, more especially, a fraction of the cDNA of HIV-2 present in the clone E2, more especially the sequence of the 3' end (LTR) and/or of the 5' end of the HIV sequence of the abovementioned clone E2, or alternatively the cDNA containing the env region, of the cDNA of the HIV-2 virus.

The probes employed in this method for diagnosis of the HIV-2 virus and in the diagnostic kits are in no way limited to the probes described above. They comprise, on the contrary, all the nucleotide sequences originating from the genome of the HIV-2 virus, of a variant of HIV-2 or of a structurally related virus, inasmuch as they enable antibodies directed against an HIV-2 to be detected in biological fluids of people capable of developing one of the forms of AIDS. Naturally, the use of nucleotide sequences originating from an HIV-2 which is initially infectious for man in nevertheless preferred.

The detection can be carried out in all manners known per se, in particular by bringing these probes into contact either with the nucleic acids obtained from cells present in these sera or other biological media, for example cerebrospinal fluids, saliva, and the like, or with these media themselves inasmuch as their nucleic acids have been rendered accessible to hybridization with these probes, this being under conditions which permit hybridization between these probes and these nucleic acids, and by detection of the hybridization which may be produced. The abovementioned diagnosis, involving hybridization reactions, can also be carried out using mixtures of probes originating, respectively, from an HIV-1 and an HIV-2, insofar as it is unnecessary to differentiate between the type of HIV virus sought.

In general, the method for diagnosis of the presence or absence of the HIV-2 virus or a variant, in samples of sera or other fluids or tissues obtained from patients suspected of being carriers of the HIV-2 virus, comprises the following stages:

1) the manufacture of a labelled probe,
2) at least one hybridization stage performed under stringent conditions, by bringing the DNA of cells in the sample from the suspect patient into contact with the said labelled probe or a suitable membrane,
3) washing of the said membrane with a solution which provides for the retention of these stringent conditions for the hybridization, and
4) the detection of the presence or absence of the HIV-2 virus by an immunodetection method.

In another preferred embodiment of the method according, to the invention, the abovementioned hybridization is performed under non-stringent conditions and the washing of the membrane is carried out under conditions adapted to those for the hybridization.

The invention relates in particular to HIV-2 viruses, characterized in that their viral RNA corresponds with a cDNA whose GAG and ENV genes comprise respectively the nucleotidic sequences which follow.

They result from the sequencing of corresponding regions of cDNA corresponding to the genome HIV-2 Rod. They are in correspondance with the aminoacids that they code.

GAGRODN

```
Met Gly Ala Arg Asn Ser Val Leu Arg Gly Lys Lys Ala Asp Glu
ATGGGCGCGAGAAACTCCGTCTTGAGAGGGAAAAAAGCAGATGAA

Leu Glu Arg Ile Arg Leu Arg Pro Gly Gly Lys Lys Lys Tyr Arg
TTAGAAAGAATCAGGTTACGGCCCGGCGGAAAGAAAAAGTACAGG

Leu Lys His Ile Val Trp Ala Ala Asn Lys Leu Asp Arg Phe Gly
CTAAAACATATTGTGTGGGCAGCGAATAAATTGGACAGATTCGGA
          100

Leu Ala Glu Ser Leu Leu Glu Ser Lys Glu Gly Cys Gln Lys Ile
TTAGCAGAGAGCCTGTTGGAGTCAAAAGAGGGTTGTCAAAAAATT

Leu Thr Val Leu Asp Pro Met Val Pro Thr Gly Ser Glu Asn Leu
CTTACAGTTTTAGATCCAATGGTACCGACAGGTTCAGAAAATTTA
                    200

Lys Ser Leu Phe Asn Thr Val Cys Val Ile Trp Cys Ile His Ala
AAAAGTCTTTTTAATACTGTCTGCGTCATTTGGTGCATACACGCA

Glu Glu Lys Val Lys Asp Thr Glu Gly Ala Lys Gln Ile Val Arg
GAAGAGAAAGTGAAAGATACTGAAGGAGCAAAACAAATAGTGCGG
                                300

Arg His Leu Val Ala Glu Thr Gly Thr Ala Glu Lys Met Pro Ser
AGACATCTAGTGGCAGAAACAGGAACTGCAGAGAAAATGCCAAGC

Thr Ser Arg Pro Thr Ala Pro Ser Ser Glu Lys Gly Gly Asn Tyr
ACAAGTAGACCAACAGCACCATCTAGCGAGAAGGGAGGAAATTAC
                                          400

Pro Val Gln His Val Gly Gly Asn Tyr Thr His Ile Pro Leu Ser
CCAGTGCAACATGTAGGCGGCAACTACACCCATATACCGCTGAGT
```

-continued

```
Pro Arg Thr Leu Asn Ala Trp Val Lys Leu Val Glu Glu Lys Lys
CCCCGAACCCTAAATGCCTGGGTAAAATTAGTAGAGGAAAAAAAG

Phe Gly Ala Glu Val Val Pro Gly Phe Gln Ala Leu Ser Glu Gly
TTCGGGGCAGAAGTAGTGCCAGGATTTCAGGCACTCTCAGAAGGC
    500

Cys Thr Pro Tyr Asp Ile  Asn Gln Met Leu Asn Cys Val Gly Asp
TGCACGCCCTATGATATCAACCAAATGCTTAATTGTGTGGGCGAC

His Gln Ala Ala Met Gln Ile  Ile  Arg Glu Ile  Ile  Asn Glu Glu
CATCAAGCAGCCATGCAGATAATCAGGGAGATTATCAATGAGGAA
            600

Ala Ala Glu Trp Asp Val Gln His Pro Ile  Pro Gly Pro Leu Pro
GCAGCAGAATGGGATGTGCAACATCCAATACCAGGCCCCTTACCA

Ala Gly Gln Leu Arg Glu Pro Arg Gly Ser Asp Ile  Ala Gly Thr
GCGGGGCAGCTTAGAGAGCCAAGGGGATCTGACATAGCAGGGACA
                            700

Thr Ser Thr Val Glu Glu Gln Ile  Gln Trp Met Phe Arg Pro Gln
ACAAGCACAGTAGAAGAACAGATCCAGTGGATGTTTAGGCCACAA

Asn Pro Val Pro Val Gly Asn Ile  Tyr Arg Arg Trp Ile  Gln Ile
AATCCTGTACCAGTAGGAAACATCTATAGAAGATGGATCCAGATA
                                    800

Gly Leu Gln Lys Cys Val Arg Met Tyr Asn Pro Thr Asn Ile  Leu
GGATTGCAGAAGTGTGTCAGGATGTACAACCCGACCAACATCCTA

Asp Ile  Lys Gln Gly Pro Lys Glu Pro Phe Gln Ser Tyr Val Asp
GACATAAAACAGGGACCAAAGGAGCCGTTCCAAAGCTATGTAGAT
                                                900

Arg Phe Tyr Lys Ser Leu Arg Ala Glu Gln Thr Asp Pro Ala Val
AGATTCTACAAAAGCTTGAGGGCAGAACAAACAGATCCAGCAGTG

Lys Asn Trp Met Thr Gln Thr Leu Leu Val Gln Asn Ala Asn Pro
AAGAATTGGATGACCCAAACACTGCTAGTACAAAATGCCAACCCA

Asp Cys Lys Leu Val Leu Lys Gly Leu Gly Met Asn Pro Thr Leu
GACTGTAAATTAGTGCTAAAAGGACTAGGGATGAACCCTACCTTA
        1000

Glu Glu Met Leu Thr Ala Cys Gln Gly Val Gly Gly Pro Gly Gln
GAAGAGATGCTGACCGCCTGTCAGGGGGTAGGTGGGCCAGGCCAG

Lys Ala Arg Leu Met Ala Glu Ala Leu Lys Glu Val Ile  Gly Pro
AAAGCTAGATTAATGGCAGAGGCCCTGAAAGAGGTCATAGGACCT
                    1100

Ala Pro Ile  Pro Phe Ala Ala Ala Gln Gln Arg Lys Ala Phe Lys
GCCCCTATCCCATTCGCAGCAGCCCAGCAGAGAAAGGCATTTAAA

Cys Trp Asn Cys Gly Lys Glu Gly His Ser Ala Arg Gln Cys Arg
TGCTGGAACTGTGGAAAGGAAGGGCACTCGGCAAGACAATGCCGA
                            1200

Ala Pro Arg Arg Gln Gly Cys Trp Lys Cys Gly Lys Pro Gly His
GCACCTAGAAGGCAGGGCTGCTGGAAGTGTGGTAAGCCAGGACAC

Ile  Met Thr Asn Cys Pro Asp Arg Gln Ala Gly Phe Leu Gly Leu
ATCATGACAAACTGCCCAGATAGACAGGCAGGTTTTTTAGGACTG
                                            1300

Gly Pro Trp Gly Lys Lys Pro Arg Asn Phe Pro Val Ala Gln Val
GGCCCTTGGGGAAAGAAGCCCCGCAACTTCCCCGTGGCCCAAGTT

Pro Gln Gly Leu Thr Pro Thr Ala Pro Pro Val Asp Pro Ala Val
CCGCAGGGGCTGACACCAACAGCACCCCCAGTGGATCCAGCAGTG
```

```
Asp Leu Leu Glu Lys Tyr Met Gln Gln Gly Lys Arg Gln Arg Glu
GATCTACTGGAGAAATATATGCAGCAAGGGAAAAGACAGAGAGAG
     1400           •          •          •          •

Gln Arg Glu Arg Pro Tyr Lys Glu Val Thr Glu Asp Leu Leu His
CAGAGAGAGAGACCATACAAGGAAGTGACAGAGGACTTACTGCAC
        •          •          •          •

Leu Glu Gln Gly Glu Thr Pro Tyr Arg Glu Pro Pro Thr Glu Asp
CTCGAGCAGGGGGAGACACCATACAGGGAGCCACCAACAGAGGAC
     •          1500         •          •          •

Leu Leu His Leu Asn Ser Leu Phe Gly Lys Asp Gln
TTGCTGCACCTCAATTCTCTCTTTGGAAAAGACCAG
        •          •          •
```

ENVRN

```
Met Met Asn Gln Leu Leu Ile  Ala Ile  Leu Leu Ala Ser Ala Cys
ATGATGAATCAGCTGCTTATTGCCATTTTATTAGCTAGTGCTTGC
        •          •          •          •

Leu Val Thr Cys Thr Gln Tyr Val Thr Val Phe Tyr Gly Val Pro
TTAGTATATTGCACCCAATATGTAACTGTTTTCTATGGCGTACCC
        •          •          •          •          •

Thr Trp Lys Asn Ala Thr Ile  Pro Leu Phe Cys Ala Thr Arg Asn
ACGTGGAAAAATGCAACCATTCCCCTCTTTTGTGCAACCAGAAAT
             100         •          •          •

Arg Asp Thr Trp Gly Thr Ile  Gln Cys Leu Pro Asp Asn Asp Asp
AGGGATACTTGGGGAACCATACAGTGCTTGCCTGACAATGATGAT
        •          •          •          •          •

Tyr Gln Glu Ile  Thr Leu Asn Val Thr Glu Ala Phe Asp Ala Trp
TATCAGGAAATAACTTTGAATGTAACAGAGGCTTTTGATGCATGG
        •          200         •          •

Asn Ans Thr Val Thr Glu Gln Ala Ile  Glu Asp Val Trp His Leu
AATAATACAGTAACAGAACAAGCAATAGAAGATGTCTGGCATCTA
        •          •          •          •          •

Phe Glu Thr Ser Ile  Lys Pro Cys Val Lys Leu Thr Pro Leu Cys
TTCGAGACATCAATAAAACCATGTGTCAAACTAACACCTTTATGT
        •          •         300         •

Val Ala Met Lys Cys Ser Ser Thr Glu Ser Ser Thr Gly Asn Asn
GTAGCAATGAAATGCAGCAGCACAGAGAGCAGCACAGGGAACAAC
        •          •          •          •          •

Thr Thr Ser Lys Ser Thr Ser Thr Thr Thr Thr Thr Pro Thr Asp
ACAACCTCAAAGAGCACAAGCACAACCACAACCACACCCACAGAC
        •          •          •         400

Gln Glu Gln Glu Ile  Ser Glu Asp Thr Pro Cys Ala Arg Ala Asp
CAGGAGCAAGAGATAAGTGAGGATACTCCATGCGCACGCGCAGAC
        •          •          •          •          •

Asn Cys Ser Gly Leu Gly Glu Glu Glu Thr Ile  Asn Cys Gln Phe
AACTGCTCAGGATTGGGAGAGGAAGAAACGATCAATTGCCAGTTC
        •          •          •          •

Asn Met Thr Gly Leu Glu Arg Asp Lys Lys Lys Gln Tyr Asn Glu
AATATGACAGGATTAGAAAGAGATAAGAAAAAACAGTATAATGAA
     500          •          •          •          •

Thr Trp Tyr Ser Lys Asp Val Val Cys Glu Thr Asn Asn Ser Thr
ACATGGTACTCAAAAGATGTGGTTTGTGAGACAAATAATAGCACA
        •          •          •          •

Asn Gln Thr Gln Cys Tyr Met Asn His Cys Asn Thr Ser Val Ile
AATCAGACCCAGTGTTACATGAACCATTGCAACACATCAGTCATC
     •          600         •          •          •

Thr Glu Ser Cys Asp Lys His Tyr Trp Asp Ala Ile  Arg Phe Arg
ACAGAATCATGTGACAAGCACTATTGGGATGCTATAAGGTTTAGA
        •          •          •          •

Tyr Cys Ala Pro Pro Gly Tyr Ala Leu Leu Arg Cys Asn Asp Thr
TACTGTGCACCACCGGGTTATGCCCTATTAAGATGTAATGATACC
     •          •         700         •          •
```

-continued

```
Asn Tyr Ser Gly Phe Ala Pro Asn Cys Ser Lys Val Val Ala Ser
AATTATTCAGGCTTTGCACCCAACTGTTCTAAAGTAGTAGCTTCT

Thr Cys Thr Arg Met Met Glu Thr Gln Thr Ser Thr Trp Phe Gly
ACATGCACCAGGATGATGGAAACGCAAACTTCCACATGGTTTGGC
                                        800

Phe Asn Gly Thr Arg Ala Glu Asn Arg Thr Tyr Ile Tyr Trp His
TTTAATGGCACTAGAGCAGAGAATAGAACATATATCTATTGGCAT

Gly Arg Asp Asn Arg Thr Ile Ile Ser Leu Asn Lys Tyr Tyr Asn
GGCAGAGATAATAGAACTATCATCAGCTTAAACAAATATTATAAT
                                        900

Leu Ser Leu His Cys Lys Arg Pro Gly Asn Lys Thr Val Lys Gln
CTCAGTTTGCATTGTAAGAGGCCAGGGAATAAGACAGTGAAACAA

Ile Met Leu Met Ser Gly His Val Phe His Ser His Tyr Gln Pro
ATAATGCTTATGTCAGGACATGTGTTTCACTCCCACTACCAGCCG

Ile Asn Lys Arg Pro Arg Gln Ala Trp Cys Trp Phe Lys Gly Lys
ATCAATAAAAGACCCAGACAAGCATGGTGCTGGTTCAAAGGCAAA
        1000

Trp Lys Asp Ala Met Gln Glu Val Lys Thr Leu Ala Lys His Pro
TGGAAAGACGCCATGCAGGAGGTGAAGACCCTTGCAAAACATCCC

Arg Tyr Arg Gly Thr Asn Asp Thr Arg Asn Ile Ser Phe Ala Ala
AGGTATAGAGGAACCAATGACACAAGGAATATTAGCTTTGCAGCG
                1100

Pro Gly Lys Gly Ser Asp Pro Glu Val Ala Tyr Met Trp Thr Asn
CCAGGAAAAGGCTCAGACCCAGAAGTAGCATACATGTGGACTAAC

Cys Arg Gly Glu Phe Leu Tyr Cys Asn Met Thr Trp Phe Leu Asn
TGCAGAGGAGAGTTTCTCTACTGCAACATGACTTGGTTCCTCAAT
                        1200

Trp Ile Glu Asn Lys Thr His Arg Asn Tyr Ala Pro Cys His Ile
TGGATAGAGAATAAGACACACCGCAATTATGCACCGTGCCATATA

Lys Gln Ile Ile Asn Thr Trp His Lys Val Gly Arg Asn Val Tyr
AAGCAAATAATTAACACATGGCATAAGGTAGGGAGAAATGTATAT
                                        1300

Leu Pro Pro Arg Glu Gly Glu Leu Ser Cys Asn Ser Thr Val Thr
TTGCCTCCCAGGGAAGGGGAGCTGTCCTGCAACTCAACAGTAACC

Ser Ile Ile Ala Asn Ile Asp Trp Gln Asn Asn Asn Gln Thr Asn
AGCATAATTGCTAACATTGACTGGCAAAACAATAATCAGACAAAC

Ile Thr Phe Ser Ala Glu Val Ala Glu Leu Tyr Arg Leu Glu Leu
ATTACCTTTAGTGCAGAGGTGGCAGAACTATACAGATTGGAGTTG
    1400

Gly Asp Tyr Lys Leu Val Glu Ile Thr Pro Ile Gly Phe Ala Pro
GGAGATTATAAATTGGTAGAAATAACACCAATTGGCTTCGCACCT

Thr Lys Glu Lys Arg Tyr Ser Ser Ala His Gly Arg His Thr Arg
ACAAAAGAAAAAAGATACTCCTCTGCTCACGGGAGACATACAAGA
        1500

Gly Val Phe Val Leu Gly Phe Leu Gly Phe Leu Ala Thr Ala Gly
GGTGTGTTCGTGCTAGGGTTCTTGGGTTTTCTCGCAACAGCAGGT

Ser Ala Met Gly Ala Arg Ala Ser Leu Thr Val Ser Ala Gln Ser
TCTGCAATGGGCGCTCGAGCGTCCCTGACCGTGTCGGCTCAGTCC
                        1600

Arg Thr Leu Leu Ala Gly Ile Val Gln Gln Gln Gln Leu Leu
CGGACTTTACTGGCCGGGATAGTGCAGCAACAGCAACAGCTGTTG
```

-continued

Asp Val Val Lys Arg Gln Gln Glu Leu Leu Arg Leu Thr Val Trp
GACGTGGTCAAGAGACAACAAGAACTGTTGCGACTGACCGTCTGG
                                    1700

Gly Thr Lys Asn Leu Gln Ala Arg Val Thr Ala Ile Glu Lys Tyr
GGAACGAAAAACCTCCAGGCAAGAGTCACTGCTATAGAGAAGTAC

Leu Gln Asp Gln Ala Arg Leu Asn Ser Trp Gly Cys Ala Phe Arg
CTACAGGACCAGGCGCGGCTAAATTCATGGGGATGTGCGTTTAGA
                                                1800

Gln Val Cys His Thr Thr Val Pro Trp Val Asn Asp Ser Leu Ala
CAAGTCTGCCACACTACTGTACCATGGGTTAATGATTCCTTAGCA

Pro Asp Trp Asp Asn Met Thr Trp Gln Glu Trp Glu Lys Gln Val
CCTGACTGGGACAATATGACGTGGCAGGAATGGGAAAAACAAGTC

Arg Tyr Leu Glu Ala Asn Ile Ser Lys Ser Leu Glu Gln Ala Gln
CGCTACCTGGAGGCAAATATCAGTAAAAGTTTAGAACAGGCACAA
       1900

Ile Gln Gln Glu Lys Asn Met Tyr Glu Leu Gln Lys Leu Asn Ser
ATTCAGCAAGAGAAAAATATGTATGAACTACAAAAATTAAATAGC

Trp Asp Ile Phe Gly Asn Trp Phe Asp Leu Thr Ser Trp Val Lys
TGGGATATTTTTGGCAATTGGTTTGACTTAACCTCCTGGGTCAAG
              2000

Tyr Ile Gln Tyr Gly Val Leu Ile Ile Val Ala Val Ile Ala Leu
TATATTCAATATGGAGTGCTTATAATAGTAGCAGTAATAGCTTTA

Arg Ile Val Ile Tyr Val Val Gln Met Leu Ser Arg Leu Arg Lys
AGAATAGTGATATATGTAGTACAAATGTTAAGTAGGCTTAGAAAG
                         2100

Gly Tyr Arg Pro Val Phe Ser Ser Pro Pro Gly Tyr Ile Gln Gln
GGCTATAGGCCTGTTTTCTCTTCCCCCCCCGGTTATATCCAACAG

Ile His Ile His Lys Asp Arg Gly Gln Pro Ala Asn Glu Glu Thr
ATCCATATCCACAAGGACCGGGGACAGCCAGCCAACGAAGAAACA
                                2200

Glu Glu Asp Gly Gly Ser Asn Gly Gly Asp Arg Tyr Trp Pro Trp
GAAGAAGACGGTGGAAGCAACGGTGGAGACAGATACTGGCCCTGG

Pro Ile Ala Tyr Ile His Phe Leu Ile Arg Gln Leu Ile Arg Leu
GCGATAGCATATATACATTTCCTGATCCGCCAGCTGATTCGCCTC

Leu Thr Arg Leu Tyr Ser Ile Cys Arg Asp Leu Leu Ser Arg Ser
TTGACCAGACTATACAGCATCTGCAGGGACTTACTATCCAGGAGC
  2300

Phe Leu Thr Leu Gln Leu Ile Tyr Gln Asn Leu Arg Asp Trp Leu
TTCCTGACCCTCCAACTCATCTACCAGAATCTCAGAGACTGGCTG

Arg Leu Arg Thr Ala Phe Leu Gln Tyr Gly Cys Glu Trp Ile Gln
AGACTTAGAACAGCCTTCTTGCAATATGGGTGCGAGTGGATCCAA
          2400

Glu Ala Phe Gln Ala Ala Ala Arg Ala Thr Arg Glu Thr Leu Ala
GAAGCATTCCAGGCCGCCGCGAGGGCTACAAGAGAGACTCTTGCG

Gly Ala Cys Arg Gly Leu Trp Arg Val Leu Glu Arg Ile Gly Arg
GGCGCGTGCAGGGGCTTGTGGAGGGTATTGGAACGAATCGGGAGG
                    2500

Gly Ile Leu Ala Val Pro Arg Arg Ile Arg Gln Gly Ala Glu Ile
GGAATACTCGCGGTTCCAAGAAGGATCAGACAGGGAGCAGAAATC

-continued

```
Ala Leu Leu *** Gly Thr Ala Val Ser Ala Gly Arg Leu Tyr Glu
GCCCTCCTGTGAGGGACGGCAGTATCAGCAGGGAGACTTTATGAA
   •          •          •          2600          •

Tyr Ser Met Glu Gly Pro Ser Ser Arg Lys Gly Glu Lys Phe Val
TACTCCATGGAAGGACCCAGCAGCAGAAAGGGAGAAAAATTTGTA
   •          •          •          •

Gln Ala Thr Lys Tyr Gly
CAGGCAACAAAATATGGA
   •          •
```

As already stated above, the invention naturally refers to all HIV-2 viruses whose RNAs possess similar characteristics, particularly GAG and ENV regions which comprise sequences having nucleotidic sequence homologies of at least 50%, preferably 70% and still more advantageously 90% with the corresponding GAG and ENV sequences of HIV-2 Rod.

The invention relates more particularly to the cDNA fragments which code, respectively, for the p16, p26 and p12 whose structures are also included in GAGRODN. In particular, it relates to the sequences extending:

from nucleotide 1 to nucleotide 405 (coding for p16);
from nucleotide 406 to nucleotide 1 155 (coding for p26); and
from nucleotide 1 156 to nucleotide 1 566 (coding for p12).

It also relates particularly to the cDNA fragment which codes for the gp140 included in ENVR and extending from the nucleotide 1 to the nucleotide 2 574.

The invention also relates to nucleotide sequences which distinguish from the preceding ones by nucleotide substitutions taking advantage of the degeneracy of the genetic code, as long as the substitutions do not involve a modification of the aminoacid sequences encoded by said nucleotide sequences.

Likewise the invention concerns proteins or glycoproteins whose aminoacid sequences correspond to those which are indicated in the preceding pages, as well as equivalent peptides, i. e. peptides which result from the preceding pages by addition, substitution or dilution of aminoacids which do not affect the overall immunological properties of said peptides.

The invention concerns especially the envelope glycoprotein which exhibits the aminoacid sequence encoded by ENVRN.

The invention also relates to an immunogenic composition characterized in that it comprises dosage units of envelope antigen, particularly the gp140 of the HIV-2 virus, such as to enable the administration of dosage units from 10 to 500, particularly from 50 to 100 mg/kg of body weight.

Finally the invention concerns a process for producing any of the above indicated proteins (p12, p16 or p26) or of the protein having the structure of gp140, or of any determined part of said proteins, which process comprises inserting the corresponding nucleic acid sequence in a vector capable of transforming a suitably chosen cellular host and to permit the expression of an insert contained in said vector, transforming said chosen host by said vector which contains said nucleic sequence, culturing the cellular host transformed by said modified vector, recovering and purifying the protein expressed.

The techniques disclosed in European patent application 85 905513.9 filed on Oct. 18, 1985 for the production of peptides or proteins consisting of expression products of nucleic acid sequences derived of the genome of HIV-1 are also applicable to the production of the above said peptides or proteins derived of HIV-2. The description of this European application is incorporated herein by reference, particularly as concerns the techniques.

As an indication, molecular weights (MP) of HIV-2 proteins are given in comparison with those of HIV-1.

| MP of HIV-2 proteins kd | | MP of HIV-I proteins kd | |
|---|---|---|---|
| entire gag | 58,3 | entire gag | 55,8 |
| p 16 | 15 | p 18 | 14,9 |
| p 26 | 27,6 | | |
| p 12 | 15,8 | | |
| env | 98,6 | env | 97,4 |
| external env | 57,4 | | |
| Transmembrane env | 41,2 | | |

HIV-2 Mir and HIV-2ROD have also been deposited in the "National Collection of Animal Cell Cultures" (ECACC) in Salisbury (Great-Britain) on Jan. 9, 1987, under accessing numbers 87 011001 and 87 011002 respectively.

Moreover, plasmids pROD35 and pROD27.5 have been deposited at the "National Collection of Industrial Bacteria" (NCIB) in Aberdeen (Great-Britain) on Jan. 9, 1987 under accessing numbers 12 398 and 12 399 respectively.

All the publications which are referred to in the present disclosure are incorporated herein by reference.

BIBLIOGRAPHIE

1—F. Barré-Sinoussi et al., Science 220, 868 (1983).
2—L. Montagnier et al., In: Human Tcell leukemia Orlymphoma viruses (Gallo, R. C., Essex, M. E., Gross, L., eds.) Cold Spring Harbor Laboratory, New York, 363 (1984).
3—M. Popovic, M. G. Sarngadharan, E. Read, R. C. Gallo, Science 224, 497 (1984).
4—J. Levy et al., Science 225, 840 (1984).
5—P. Sonigo et al., Cell 42, 369 (1985).
7—J. W. Curran et al., Science 229, 1352 (1985).
8—A. Ellrodt et al., Lancet i, 1383 (1984).
9—P. Piot et al., Lancet ii, 65 (1984).
10—F. Brun-Vezinet et al., Science 226, 453 (1984).
11—N. Clumeck et al., N. Engl. J. Med. 313, 182 (1985).
12—A. B. Rabson and M. A. Martin, Cell 40, 477 (1985).
13—S. Benn et al., Science 230, 949 (1985).
14—M. Alizon, Manuscript in preparation.
15—F. Brun-Vezinet, Unpublished data.
16—M. D. Daniel et al., Science 228, 1201 (1985).
17—P. J. Kanki et al., Science 228, 1199 (1985).
18—N. L. Letwin et al., Science 230, 71 (1985).
19—A. Gatzar et al., Blood 55, 409 (1980).
20—D. Klatzmann et al., Science 225, 59 (1984).
21—L. Montagnier et al., Virology 144, 283 (1985).
22—J. S. Allan et al., Science 228, 1091 (1985).
23—F. CHIVel, Manuscript in preparation.
24—F. diMarzo Veronese et al., Science 229, 1402 (1985).

25—V. S. Kalyanaraman et al., Science 218, 571 (1982).
26—I. S. Y. Chen, J. McLaughlin, J. C. Gasson, S. C. Clark and D. W. Golde, Nature 305, 502 (1983).
27—F. Barin et al., Lancet ii, 1387 (1985).
28—P. J. Kanki, J. Alroy, M. Essex, Science 230, 951 (1985).
29—H. Towbin et al., Proc. Natl. Acad. Sci. USA 76, 4350 (1979).
30—S. Wain-Hobson, P. Sonigo, O. Danos, S. Cole et M. Alizon, Cell 40, 9 (1985).
31—M. Alizon et al., Nature 312, 757 (1984).

We claim:

1. An in vitro diagnostic assay for the detection of antibodies specific for human immunodeficiency virus type 1 (HIV-1), type 2 (HIV-2), or both types 1 and 2 in a biological sample, comprising:
(a) contacting the biological sample with one or more HIV-2 peptides selected from the group consisting of:
(1) a peptide encoded by the HIV-2 gag gene, wherein said peptide comprises the following sequence:

Met Gly Ala Arg Asn Ser Val Leu Arg Gly Lys

Lys Ala Asp Glu Leu

Glu Arg Ile Arg Leu Arg Pro Gly Gly Lys Lys

Lys Tyr Arg Leu Lys

His Ile Val Trp Ala Ala Asn Lys Leu Asp Arg

Phe Gly Leu Ala Glu

Ser Leu Leu Glu Ser Lys Glu Gly Cys Gln Lys

Ile Leu Thr Val Leu

Asp Pro Met Val Pro Thr Gly Ser Glu Asn Leu

Lys Ser Leu Phe Asn

Thr Val Cys Val Ile Trp Cys Ile His Ala Glu

Glu Lys Val Lys Asp

Thr Glu Gly Ala Lys Gln Ile Val Arg Arg His

Leu Val Ala Glu Thr

Gly Thr Ala Glu Lys Met Pro Ser Thr Ser Arg

Pro Thr Ala Pro Ser

Ser Glu Lys Gly Gly Asn Tyr Pro Val Gln His

Val Gly Gly Asn Tyr

Thr His Ile Pro Leu Ser Pro Arg Thr Leu Asn

Ala Trp Val Lys Leu

-continued

Val Glu Glu Lys Lys Phe Gly Ala Glu Val Val

Pro Gly Phe Gln Ala
Leu Ser Glu Gly Cys Thr Pro Tyr Asp Ile Asn
Gln Met Leu Asn Cys
Val Gly Asp His Gln Ala Ala Met Gln Ile Ile
Arg Glu Ile Ile Asn
Glu Glu Ala Ala Glu Trp Asp Val Gln His Pro
Ile Pro Gly Pro Leu
Pro Ala Gly Gln Leu Arg Glu Pro Arg Gly Ser
Asp Ile Ala Gly Thr
Thr Ser Thr Val Glu Glu Gln Ile Gln Trp Met
Phe Arg Pro Gln Asn
Pro Val Pro Val Gly Asn Ile Tyr Arg Arg Trp
Ile Gln Ile Gly Leu
Gln Lys Cys Val Arg Met Tyr Asn Pro Thr Asn
Ile Leu Asp Ile Lys
Gln Gly Pro Lys Glu Pro Phe Gln Ser Tyr Val
Asp Arg Phe Tyr Lys
Ser Leu Arg Ala Glu Gln Thr Asp Pro Ala Val
Lys Asn Trp Met Thr
Gln Thr Leu Leu Val Gln Asn Ala Asn Pro Asp
Cys Lys Leu Val Leu
Lys Gly Leu Gly Met Asn Pro Thr Leu Glu Glu
Met Leu Thr Ala Cys
Gln Gly Val Gly Gly Pro Gly Gln Lys Ala Arg
Leu Met Ala Glu Ala
Leu Lys Glu Val Ile Gly Pro Ala Pro Ile Pro
Phe Ala Ala Ala Gln

41

-continued

| | | | | | | | | | |
|---|---|---|---|---|---|---|---|---|---|
| Gln | Arg | Lys | Ala | Phe | Lys | Cys | Trp | Asn | Cys | Gly |
| | | | | | Lys | Glu | Gly | His | Ser |
| Ala | Arg | Gln | Cys | Arg | Ala | Pro | Arg | Arg | Gln | Gly |
| | | | | | Cys | Trp | Lys | Cys | Gly |
| Lys | Pro | Gly | His | Ile | Met | Thr | Asn | Cys | Pro | Asp |
| | | | | | Arg | Gln | Ala | Gly | Phe |
| Leu | Gly | Leu | Gly | Pro | Trp | Gly | Lys | Lys | Pro | Arg |
| | | | | | Asn | Phe | Pro | Val | Ala |
| Gln | Val | Pro | Gln | Gly | Leu | Thr | Pro | Thr | Ala | Pro |
| | | | | | Pro | Val | Asp | Pro | Ala |
| Val | Asp | Leu | Leu | Glu | Lys | Tyr | Met | Gln | Gln | Gly |
| | | | | | Lys | Arg | Gln | Arg | Glu |
| Gln | Arg | Glu | Arg | Pro | Tyr | Lys | Glu | Val | Thr | Glu |
| | | | | | Asp | Leu | Leu | His | Leu |
| Glu | Gln | Gly | Glu | Thr | Pro | Tyr | Arg | Glu | Pro | Pro |
| | | | | | Thr | Glu | Asp | Leu | Leu |
| His | Leu | Asn | Ser | Leu | Phe | Gly | Lys | Asp | Gln; | |

(2) a peptide encoded by the HIV-2 env gene, wherein said peptide comprises the following sequence:

Met Met Asn Gln Leu Leu Ile Ala Ile Leu Leu Ala Ser Ala Cys Leu Val Tyr Cys Thr Gln Tyr Val Thr Val Phe Tyr Gly Val Pro Thr Trp Lys Asn Ala Thr Thr Pro Leu Phe Cys Ala Thr Arg Asn Arg Asp Thr Trp Gly Thr Ile Gln Cys Leu Pro Asp Asn Asp Asp Tyr Gln Glu Ile Thr Leu Asn Val Thr Glu Ala Phe Asp Ala Trp Asn Asn Thr Val Thr

-continued

Glu Gln Ala Ile Glu Asp Val Trp His Leu Phe Glu Thr Ser Ile Lys Pro Cys Val Lys Leu Thr Pro Leu Cys Val Ala Met Lys Cys Ser Ser Thr Glu Ser Ser Thr Gly Asn Asn Thr Thr Ser Lys Ser Thr Ser Thr Thr Thr Thr Thr Pro Thr Asp Gln Glu Gln Glu Ile Ser Glu Asp Thr Pro Cys Ala Arg Ala Asp Asn Cys Ser Gly Leu Gly Glu Glu Glu Thr Ile Asn Cys Gln Phe Asn Met Thr Gly leu Glu Arg Asp Lys Lys Lys Gln Tyr Asn Glu Thr Trp Tyr Ser Lys Asp Val Val Cys Glu Thr Asn Asn Ser Thr Asn Gln Thr Gln Cys Tyr Met Asn His Cys Asn Thr Ser Val Ile Thr Glu Ser Cys Asp Lys His Tyr Trp Asp Ala Ile Arg Phe Arg Tyr Cys Ala Pro Pro Gly Tyr Ala Leu Leu Arg Cys Asn Asp Thr Asn Tyr Ser Gly Phe Ala Pro Asn Cys Ser Lys Val Val Ala Ser Thr Cys Thr Arg Met Met Glu Thr Gln Thr Ser Thr Trp Phe Gly Phe Asn Gly Thr Arg Ala Glu Asn Arg Thr Tyr Ile Tyr Trp His Gly Arg Asp Asn Arg Thr Ile Ile Ser Leu Asn Lys Tyr Tyr Asn Leu Ser Leu His

43

-continued

Cys Lys Arg Pro Gly Asn Lys Thr

Val Lys Gln Ile Met Leu Met Ser
Gly His Val Phe His Ser His Tyr
        Gln Pro Ile Asn Lys Arg Pro Arg
Gln Ala Trp Cys Trp Phe Lys Gly
        Lys Trp Lys Asp Ala Met Gln Glu
Val Lys Glu Thr Leu Ala Lys His
        Pro Arg Tyr Arg Gly Thr Asn Asp
Thr Arg Asn Ile Ser Phe Ala Ala
        Pro Gly Lys Gly Ser Asp Pro Glu
Val Ala Tyr Met Trp Thr Asn Cys
        Arg Gly Glu Phe Leu Tyr Cys Asn
Met Thr Trp Phe Leu Asn Trp Ile
        Glu Asn Lys Thr His Arg Asn Tyr
Ala Pro Cys His Ile Lys Gln Ile
        Ile Asn Thr Trp His Lys Val Gly
Arg Asn Val Tyr Leu Pro Pro Arg
        Glu Gly Glu Leu Ser Cys Asn Ser
Thr Val Thr Ser Ile Ile Ala Asn
        Ile Asp Trp Gln Asn Asn Asn Gln
Thr Asn Ile Thr Phe Ser Ala Glu
        Val Ala Glu Leu Tyr Arg Leu Glu
Leu Gly Asp Tyr Lys Leu Val Glu
        Ile Thr Pro Ile Gly Phe Ala Pro
Thr Lys Glu Lys Arg Tyr Ser Ser
        Ala His Gly Arg His Thr Arg Gly
Val Phe Val Leu Gly Phe Leu Gly
        Phe Leu Ala Thr Ala Gly Ser Ala

44

-continued

Met Gly Ala Ala Ser Leu Thr Val

Ser Ala Gln Ser Arg Thr Leu Leu
Ala Gly Ile Val Gln Gln Gln Gln
        Gln Leu Leu Asp Val Val Lys Arg
Gln Gln Glu Leu Leu Arg Leu Thr
        Val Trp Gly Thr Lys Asn Leu Gln
Ala Arg Val Thr Ala Ile Glu Lys
        Tyr Leu Gln Asp Gln Ala Arg Leu
Asn Ser Trp Gly Cys Ala Phe Arg
        Gln Val Cys His Thr Thr Val Pro
Trp Val Asn Asp Ser Leu Ala Pro
        Asp Trp Asp Asn Met Thr Trp Gln
Glu Trp Glu Lys Gln Val Arg Tyr
        Leu Glu Ala Asn Ile Ser Lys Ser
Leu Glu Gln Ala Gln Ile Gln Gln
        Glu Lys Asn Met Tyr Glu Leu Gln
Lys Leu Asn Ser Trp Asp Ile Phe
        Gly Asn Trp Phe Asp Leu Thr Ser
Trp Val Lys Tyr Ile Gln Tyr Gly
        Val Leu Ile Ile Val Ala Val Ile
Ala Leu Arg Ile Val Ile Tyr Val
        Val Gln Met Leu Ser Arg Leu Arg
Lys Gly Tyr Arg Pro Val Phe Ser
        Ser Pro Pro Gly Tyr Ile Gln Gln
Ile His Ile His Lys Asp Arg Gly
        Gln Pro Ala Asn Glu Glu Thr Glu
Glu Asp Gly Gly Ser Asn Gly Gly
        Asp Arg Tyr Trp Pro Trp Pro Ile

Ala Tyr Ile His Phe Leu Ile Arg

Gln Leu Ile Arg Leu Leu Thr Arg

Gln Leu Ile Tyr Gln Asn Leu Arg

Asp Trp Leu Arg Leu Arg Thr Ala

Phe Leu Gln Tyr Gly Cys Glu Trp

Ile Gln Glu Ala Phe Gln Ala Ala

Ala Arg Ala Thr Arg Glu Thr Leu

Ala Gly Ala Cys Arg Gly Leu Trp

Arg Val Leu Glu Arg Ile Gly Arg

Gly Ile Leu Ala Val Pro Arg Arg

Ile Arg Gln Gly Ala Glu Ile Ala

Leu Leu;

(3) a p16 peptide encoded by the HIV-2 gag gene, wherein said peptide comprises the following sequence:

Met Gly Ala Arg Asn Ser Val Leu Arg Gly Lys

Lys Ala Asp Glu Leu

Glu Arg Ile Arg Leu Arg Pro Gly Gly Lys Lys

Lys Tyr Arg Leu Lys

His Ile Val Trp Ala Ala Asn Lys Leu Asp Arg

Phe Gly Leu Ala Glu

Ser Leu Leu Glu Ser Lys Glu Gly Cys Gln Lys

Ile Leu Thr Val Leu

Asp Pro Met Val Pro Thr Gly Ser Glu Asn Leu

Lys Ser Leu Phe Asn

Thr Val Cys Val Ile Trp Cys Ile His Ala Glu

Glu Lys Val Lys Asp

Thr Glu Gly Ala Lys Gln Ile Val Arg Arg His

Leu Val Ala Glu Thr

Gly Thr Ala Glu Lys Met Pro Ser Thr Ser Arg

Pro Thr Ala Pro Ser

Ser Glu Lys Gly Gly Asn Tyr;

(4) a p26 peptide encoded by the HIV-2 gag gene, wherein said peptide comprises the following sequence:

Pro Val Gln His Val Gly Gly Asn Tyr Thr His

Ile Pro Leu Ser Pro

Arg Thr Leu Asn Ala Trp Val Lys Leu Val Glu

Glu Lys Lys Phe Gly Ala Glu Val Val Pro Gly Phe Gln Ala Leu Ser Glu Gly Cys Thr Pro Tyr Asp Ile Asn Gln Met Leu Asn Cys Val Gly Asp His Gln Ala Ala Met Gln Ile Ile Arg Glu Ile Ile Asn Glu Glu Ala Ala Glu Trp Asp Val Gln His Pro Ile Pro Gly Pro Leu Pro Ala Gly Gln Leu Arg Glu Pro Arg Gly Ser Asp Ile Ala Gly Thr Thr Ser Thr Val Glu Glu Gln Ile Gln Trp Met Phe Arg Pro Gln Asn Pro Val Pro Val Gly Asn Ile Tyr Arg Arg Trp Ile Gln Ile Gly Leu Gln Lys Cys Val Arg Met Tyr Asn Pro Thr Asn Ile Leu Asp Ile Lys Gln Gly Pro Lys Glu Pro Phe Gln Ser Tyr Val Asp Arg Phe Tyr Lys Ser Leu Arg Ala Glu Gln Thr Asp Pro Ala Val Lys Asn Trp Met Thr Gln Thr

-continued

```
                          Leu Leu Val Gln Asn

Ala Asn Pro Asp Cys Lys Leu Val Leu Lys Gly

Leu Gly Met Asn Pro

Thr Leu Glu Glu Met Leu Thr Ala Cys Gln Gly

Val Gly Gly Pro Gly

Gln Lys Ala Arg Leu Met Ala Glu Ala Leu Lys

Glu Ile Ile Gly Pro

Ala Pro Ile Pro Phe Ala Ala Ala Gln Gln; and
```

(5) a p12 peptide encoded by the HIV-2 gag gene, wherein said peptide comprises the following sequence:

```
Arg Lys Ala Phe Lys Cys Trp Asn Cys Gly Lys

Glu Gly His Ser Ala

Arg Gln Cys Arg Ala Pro Arg Arg Gln Gly Cys

Trp Lys Cys Gly Lys

Pro Gly His Ile Met Thr Asn Cys Pro Asp Arg

Gln Ala Gly Phe Leu

Gly Leu Gly Pro Trp Gly Lys Lys Pro Arg Asn

Phe Pro Val Ala Gln

Val Pro Gln Gly Leu Thr Pro Thr Ala Pro Pro

Val Asp Pro Ala Val

Asp Leu Leu Glu Lys Tyr Met Gln Gln Gly Lys

Arg Gln Arg Glu Gln

Arg Glu Arg Pro Tyr Lys Glu Val Thr Glu Asp

Leu Leu His Leu Glu

Gln Gly Glu Thr Pro Tyr Arg Glu Pro Pro Thr

Glu Asp Leu Leu His

Leu Asn Ser Leu Phe Gly Lys Asp Gln;
```

(b) contacting said biological sample with one or more HIV-1 peptides; and (c) detecting the formation of antigen-antibody complexes between said one or more peptides and antibodies present in said biological sample.

2. The assay of claim 1, wherein said sample is also contacted with one or more proteins selected from the group consisting of external env glycoprotein of HIV-2 and transmembrane env protein of HIV-2.

3. The assay of claim 1, wherein said one or more peptides of HIV-1 is selected from the group consisting of p25, p18, gp110, and gp41 of HIV-1.

4. The assay according to any one of claims 1, 2, or 3, wherein the formation of antigen-antibody complex is detected by employing a process selected from the group consisting of radioimmunoassay, radioimmunoprecipitation assay, immunofluorescence assay, enzyme-linked immunosorbent assay, and Western blot.

5. The assay according to claim 4, wherein said peptide or protein is labeled with a label selected from the group consisting of an enzyme label, a fluorescent label, and a radioactive label.

6. An in vitro diagnostic kit for the detection of antibodies specific for human immunodeficiency virus type 1 (HIV-1), type 2, or both type 1 and 2 in a biological sample, comprising:

(a) a peptide composition comprising one or more HIV-2 peptides selected from the group consisting of:

(1) a peptide encoded by the HIV-2 gag gene, wherein said peptide comprises the following sequence:

```
Met Gly Ala Arg Asn Ser Val Leu Arg Gly Lys

Lys Ala Asp Glu Leu

Glu Arg Ile Arg Leu Arg Pro Gly Gly Lys Lys

Lys Tyr Arg Leu Lys

His Ile Val Trp Ala Ala Asn Lys Leu Asp Arg

Phe Gly Leu Ala Glu

Ser Leu Leu Glu Ser Lys Glu Gly Cys Gln Lys

Ile Leu Thr Val Leu

Asp Pro Met Val Pro Thr Gly Ser Glu Asn Leu

Lys Ser Leu Phe Asn

Thr Val Cys Val Ile Trp Cys Ile His Ala Glu

Glu Lys Val Lys Asp

Thr Glu Gly Ala Lys Gln Ile Val Arg Arg His

Leu Val Ala Glu Thr

Gly Thr Ala Glu Lys Met Pro Ser Thr Ser Arg

Pro Thr Ala Pro Ser
```

```
Ser Glu Lys Gly Gly Asn Tyr Pro Val Gln His
                                Val Gly Gly Asn Tyr     5
Thr His Ile Pro Leu Ser Pro Arg Thr Leu Asn
                                Ala Trp Val Lys Leu    10
Val Glu Glu Lys Lys Phe Gly Ala Glu Val Val
                                Pro Gly Phe Gln Ala
Leu Ser Glu Gly Cys Thr Pro Tyr Asp Ile Asn            15
                                Gln Met Leu Asn Cys
Val Gly Asp His Gln Ala Ala Met Gln Ile Ile            20
                                Arg Glu Ile Ile Asn
Glu Glu Ala Ala Glu Trp Asp Val Gln His Pro            25
                                Ile Pro Gly Pro Leu
Pro Ala Gly Gln Leu Arg Glu Pro Arg Gly Ser            30
                                Asp Ile Ala Gly Thr
Thr Ser Thr Val Glu Glu Gln Ile Gln Trp Met            35
                                Phe Arg Pro Gln Asn
Pro Val Pro Val Gly Asn Ile Tyr Arg Arg Trp            40
                                Ile Gln Ile Gly Leu
Gln Lys Cys Val Arg Met Tyr Asn Pro Thr Asn            45
                                Ile Leu Asp Ile Lys
Gln Gly Pro Lys Glu Pro Phe Gln Ser Tyr Val
                                Asp Arg Phe Tyr Lys    50
Ser Leu Arg Ala Glu Gln Thr Asp Pro Ala Val
                                Lys Asn Trp Met Thr    55
Gln Thr Leu Leu Val Gln Asn Ala Asn Pro Asp
```

```
                                Cys Lys Leu Val Leu
Lys Gly Leu Gly Met Asn Pro Thr Leu Glu Glu
                                Met Leu Thr Ala Cys
Gln Gly Val Gly Gly Pro Gly Gln Lys Ala Arg
                                Leu Met Ala Glu Ala
Leu Lys Glu Val Ile Gly Pro Ala Pro Ile Pro
                                Phe Ala Ala Ala Gln
Gln Arg Lys Ala Phe Lys Cys Trp Asn Cys Gly
                                Lys Glu Gly His Ser
Ala Arg Gln Cys Arg Ala Pro Arg Arg Gln Gly
                                Cys Trp Lys Cys Gly
Lys Pro Gly His Ile Met Thr Asn Cys Pro Asp
                                Arg Gln Ala Gly Phe
Leu Gly Leu Gly Pro Trp Gly Lys Lys Pro Arg
                                Asn Phe Pro Val Ala
Gln Val Pro Gln Gly Leu Thr Pro Thr Ala Pro
                                Pro Val Asp Pro Ala
Val Asp Leu Leu Glu Lys Tyr Met Gln Gln Gly
                                Lys Arg Gln Arg Glu
Gln Arg Glu Arg Pro Tyr Lys Glu Val Thr Glu
                                Asp Leu Leu His Leu
Glu Gln Gly Glu Thr Pro Tyr Arg Glu Pro Pro
                                Thr Glu Asp Leu Leu
His Leu Asn Ser Leu Phe Gly Lys Asp Gln;
```

(2) a peptide encoded by the HIV-2 env gene, wherein said peptide comprises the following sequence:

```
Met Met Asn Gln Leu Leu Ile Ala Ile Leu Leu Ala Ser Ala Cys Leu
Val Tyr Cys Thr Gln Tyr Val Thr Val Phe Tyr Gly Val Pro Thr Trp
```

-continued

| Lys | Asn | Ala | Thr | Thr | Pro | Leu | Phe | Cys | Ala | Thr | Arg | Asn | Arg | Asp | Thr |
|-----|-----|-----|-----|-----|-----|-----|-----|-----|-----|-----|-----|-----|-----|-----|-----|
| Trp | Gly | Thr | Ile | Gln | Cys | Leu | Pro | Asp | Asn | Asp | Asp | Tyr | Gln | Glu | Ile |
| Thr | Leu | Asn | Val | Thr | Glu | Ala | Phe | Asp | Ala | Trp | Asn | Asn | Thr | Val | Thr |
| Glu | Gln | Ala | Ile | Glu | Asp | Val | Trp | His | Leu | Phe | Glu | Thr | Ser | Ile | Lys |
| Pro | Cys | Val | Lys | Leu | Thr | Pro | Leu | Cys | Val | Ala | Met | Lys | Cys | Ser | Ser |
| Thr | Glu | Ser | Ser | Thr | Gly | Asn | Asn | Thr | Thr | Ser | Lys | Ser | Thr | Ser | Thr |
| Thr | Thr | Thr | Thr | Pro | Thr | Asp | Gln | Glu | Gln | Glu | Ile | Ser | Glu | Asp | Thr |
| Pro | Cys | Ala | Arg | Ala | Asp | Asn | Cys | Ser | Gly | Leu | Gly | Glu | Glu | Glu | Thr |
| Ile | Asn | Cys | Gln | Phe | Asn | Met | Thr | Gly | leu | Glu | Arg | Asp | Lys | Lys | Lys |
| Gln | Tyr | Asn | Glu | Thr | Trp | Tyr | Ser | Lys | Asp | Val | Val | Cys | Glu | Thr | Asn |
| Asn | Ser | Thr | Asn | Gln | Thr | Gln | Cys | Tyr | Met | Asn | His | Cys | Asn | Thr | Ser |
| Val | Ile | Thr | Glu | Ser | Cys | Asp | Lys | His | Tyr | Trp | Asp | Ala | Ile | Arg | Phe |
| Arg | Tyr | Cys | Ala | Pro | Pro | Gly | Tyr | Ala | Leu | Leu | Arg | Cys | Asn | Asp | Thr |
| Asn | Tyr | Ser | Gly | Phe | Ala | Pro | Asn | Cys | Ser | Lys | Val | Val | Ala | Ser | Thr |
| Cys | Thr | Arg | Met | Met | Glu | Thr | Gln | Thr | Ser | Thr | Trp | Phe | Gly | Phe | Asn |
| Gly | Thr | Arg | Ala | Glu | Asn | Arg | Thr | Tyr | Ile | Tyr | Trp | His | Gly | Arg | Asp |
| Asn | Arg | Thr | Ile | Ile | Ser | Leu | Asn | Lys | Tyr | Tyr | Asn | Leu | Ser | Leu | His |
| Cys | Lys | Arg | Pro | Gly | Asn | Lys | Thr | Val | Lys | Gln | Ile | Met | Leu | Met | Ser |
| Gly | His | Val | Phe | His | Ser | His | Tyr | Gln | Pro | Ile | Asn | Lys | Arg | Pro | Arg |
| Gln | Ala | Trp | Cys | Trp | Phe | Lys | Gly | Lys | Trp | Lys | Asp | Ala | Met | Gln | Glu |
| Val | Lys | Glu | Thr | Leu | Ala | Lys | His | Pro | Arg | Tyr | Arg | Gly | Thr | Asn | Asp |
| Thr | Arg | Asn | Ile | Ser | Phe | Ala | Ala | Pro | Gly | Lys | Gly | Ser | Asp | Pro | Glu |
| Val | Ala | Tyr | Met | Trp | Thr | Asn | Cys | Arg | Gly | Glu | Phe | Leu | Tyr | Cys | Asn |
| Met | Thr | Trp | Phe | Leu | Asn | Trp | Ile | Glu | Asn | Lys | Thr | His | Arg | Asn | Tyr |
| Ala | Pro | Cys | His | Ile | Lys | Gln | Ile | Ile | Asn | Thr | Trp | His | Lys | Val | Gly |
| Arg | Asn | Val | Tyr | Leu | Pro | Pro | Arg | Glu | Gly | Glu | Leu | Ser | Cys | Asn | Ser |
| Thr | Val | Thr | Ser | Ile | Ile | Ala | Asn | Ile | Asp | Trp | Gln | Asn | Asn | Asn | Gln |
| Thr | Asn | Ile | Thr | Phe | Ser | Ala | Glu | Val | Ala | Glu | Leu | Tyr | Arg | Leu | Glu |
| Leu | Gly | Asp | Tyr | Lys | Leu | Val | Glu | Ile | Thr | Pro | Ile | Gly | Phe | Ala | Pro |
| Thr | Lys | Glu | Lys | Arg | Tyr | Ser | Ser | Ala | His | Gly | Arg | His | Thr | Arg | Gly |
| Val | Phe | Val | Leu | Gly | Phe | Leu | Gly | Phe | Leu | Ala | Thr | Ala | Gly | Ser | Ala |
| Met | Gly | Ala | Ala | Ser | Leu | Thr | Val | Ser | Ala | Gln | Ser | Arg | Thr | Leu | Leu |
| Ala | Gly | Ile | Val | Gln | Gln | Gln | Gln | Leu | Leu | Asp | Val | Val | Lys | Arg |
| Gln | Gln | Glu | Leu | Leu | Arg | Leu | Thr | Val | Trp | Gly | Thr | Lys | Asn | Leu | Gln |
| Ala | Arg | Val | Thr | Ala | Ile | Glu | Lys | Tyr | Leu | Gln | Asp | Gln | Ala | Arg | Leu |
| Asn | Ser | Trp | Gly | Cys | Ala | Phe | Arg | Gln | Val | Cys | His | Thr | Thr | Val | Pro |
| Trp | Val | Asn | Asp | Ser | Leu | Ala | Pro | Asp | Trp | Asp | Asn | Met | Thr | Trp | Gln |
| Glu | Trp | Glu | Lys | Gln | Val | Arg | Tyr | Leu | Glu | Ala | Asn | Ile | Ser | Lys | Ser |
| Leu | Glu | Gln | Ala | Gln | Ile | Gln | Gln | Glu | Lys | Asn | Met | Tyr | Glu | Leu | Gln |
| Lys | Leu | Asn | Ser | Trp | Asp | Ile | Phe | Gly | Asn | Trp | Phe | Asp | Leu | Thr | Ser |
| Trp | Val | Lys | Tyr | Ile | Gln | Tyr | Gly | Val | Leu | Ile | Ile | Val | Ala | Val | Ile |
| Ala | Leu | Arg | Ile | Val | Ile | Tyr | Val | Val | Gln | Met | Leu | Ser | Arg | Leu | Arg |
| Lys | Gly | Tyr | Arg | Pro | Val | Phe | Ser | Ser | Pro | Pro | Gly | Tyr | Ile | Gln | Gln |
| Ile | His | Ile | His | Lys | Asp | Arg | Gly | Gln | Pro | Ala | Asn | Glu | Glu | Thr | Glu |

-continued

| | | | | | | | | | | | | | |
|---|---|---|---|---|---|---|---|---|---|---|---|---|---|
| Glu | Asp | Gly | Gly | Ser | Asn | Gly | Gly | Asp | Arg | Tyr | Trp | Pro | Trp | Pro | Ile |
| Ala | Tyr | Ile | His | Phe | Leu | Ile | Arg | Gln | Leu | Ile | Arg | Leu | Leu | Thr | Arg |
| Leu | Tyr | Ser | Ile | Cys | Arg | Asp | Leu | Leu | Ser | Arg | Ser | Phe | Leu | Thr | Leu |
| Gln | Leu | Ile | Tyr | Gln | Asn | Leu | Arg | Asp | Trp | Leu | Arg | Leu | Arg | Thr | Ala |
| Phe | Leu | Gln | Tyr | Gly | Cys | Glu | Trp | Ile | Gln | Glu | Ala | Phe | Gln | Ala | Ala |
| Ala | Arg | Ala | Thr | Arg | Glu | Thr | Leu | Ala | Gly | Ala | Cys | Arg | Gly | Leu | Trp |
| Arg | Val | Leu | Glu | Arg | Ile | Gly | Arg | Gly | Ile | Leu | Ala | Val | Pro | Arg | Arg |
| Ile | Arg | Gln | Gly | Ala | Glu | Ile | Ala | Leu | Leu; | | | | | | |

(3) a p16 peptide encoded by the HIV-2 gag gene, wherein said peptide comprises the following sequence:

| | | | | | | | | | | | | | |
|---|---|---|---|---|---|---|---|---|---|---|---|---|---|
| Met | Gly | Ala | Arg | Asn | Ser | Val | Leu | Arg | Gly | Lys | Lys | Ala | Asp | Glu | Leu |
| Glu | Arg | Ile | Arg | Leu | Arg | Pro | Gly | Gly | Lys | Lys | Lys | Tyr | Arg | Leu | Lys |
| His | Ile | Val | Trp | Ala | Ala | Asn | Lys | Leu | Asp | Arg | Phe | Gly | Leu | Ala | Glu |
| Ser | Leu | Leu | Glu | Ser | Lys | Glu | Gly | Cys | Gln | Lys | Ile | Leu | Thr | Val | Leu |
| Asp | Pro | Met | Val | Pro | Thr | Gly | Ser | Glu | Asn | Leu | Lys | Ser | Leu | Phe | Asn |
| Thr | Val | Cys | Val | Ile | Trp | Cys | Ile | His | Ala | Glu | Glu | Lys | Val | Lys | Asp |
| Thr | Glu | Gly | Ala | Lys | Gln | Ile | Val | Arg | Arg | His | Leu | Val | Ala | Glu | Thr |
| Gly | Thr | Ala | Glu | Lys | Met | Pro | Ser | Thr | Ser | Arg | Pro | Thr | Ala | Pro | Ser |
| Ser | Glu | Lys | Gly | Gly | Asn | Tyr; | | | | | | | | | |

(4) a p26 peptide encoded by the HIV-2 gag gene, wherein said peptide comprises the following sequence:

| | | | | | | | | | | | | | |
|---|---|---|---|---|---|---|---|---|---|---|---|---|---|
| Pro | Val | Gln | His | Val | Gly | Gly | Asn | Tyr | Thr | His | Ile | Pro | Leu | Ser | Pro |
| Arg | Thr | Leu | Asn | Ala | Trp | Val | Lys | Leu | Val | Glu | Glu | Lys | Lys | Phe | Gly |
| Ala | Glu | Val | Val | Pro | Gly | Phe | Gln | Ala | Leu | Ser | Glu | Gly | Cys | Thr | Pro |
| Tyr | Asp | Ile | Asn | Gln | Met | Leu | Asn | Cys | Val | Gly | Asp | His | Gln | Ala | Ala |
| Met | Gln | Ile | Ile | Arg | Glu | Ile | Ile | Asn | Glu | Glu | Ala | Ala | Glu | Trp | Asp |
| Val | Gln | His | Pro | Ile | Pro | Gly | Pro | Leu | Pro | Ala | Gly | Gln | Leu | Arg | Glu |
| Pro | Arg | Gly | Ser | Asp | Ile | Ala | Gly | Thr | Thr | Ser | Thr | Val | Glu | Glu | Gln |
| Ile | Gln | Trp | Met | Phe | Arg | Pro | Gln | Asn | Pro | Val | Pro | Val | Gly | Asn | Ile |
| Tyr | Arg | Arg | Trp | Ile | Gln | Ile | Gly | Leu | Gln | Lys | Cys | Val | Arg | Met | Tyr |
| Asn | Pro | Thr | Asn | Ile | Leu | Asp | Ile | Lys | Gln | Gly | Pro | Lys | Glu | Pro | Phe |
| Gln | Ser | Tyr | Val | Asp | Arg | Phe | Tyr | Lys | Ser | Leu | Arg | Ala | Glu | Gln | Thr |
| Asp | Pro | Ala | Val | Lys | Asn | Trp | Met | Thr | Gln | Thr | Leu | Leu | Val | Gln | Asn |
| Ala | Asn | Pro | Asp | Cys | Lys | Leu | Val | Leu | Lys | Gly | Leu | Gly | Met | Asn | Pro |
| Thr | Leu | Glu | Glu | Met | Leu | Thr | Ala | Cys | Gln | Gly | Val | Gly | Gly | Pro | Gly |
| Gln | Lys | Ala | Arg | Leu | Met | Ala | Glu | Ala | Leu | Lys | Glu | Val | Ile | Gly | Pro |
| Ala | Pro | Ile | Pro | Phe | Ala | Ala | Ala | Gln | Gln; | and | | | | | |

(5) a p12 peptide encoded by the HIV-2 gag gene, wherein said peptide comprises the following sequence:

Arg Lys Ala Phe Lys Cys Trp Asn Cys Gly Lys Glu Gly His Ser Ala
Arg Gln Cys Arg Ala Pro Arg Arg Gln Gly Cys Trp Lys Cys Gly Lys
Pro Gly His Ile Met Thr Asn Cys Pro Asp Arg Gln Ala Gly Phe Leu
Gly Leu Gly Pro Trp Gly Lys Lys Pro Arg Asn Phe Pro Val Ala Gln
Val Pro Gln Gly Leu Thr Pro Thr Ala Pro Pro Val Asp Pro Ala Val
Asp Leu Leu Glu Lys Tyr Met Gln Gln Gly Lys Arg Gln Arg Glu Gln
Arg Glu Arg Pro Tyr Lys Glu Val Thr Glu Asp Leu Leu His Leu Glu
Gln Gly Glu Thr Pro Tyr Arg Glu Pro Pro Thr Glu Asp Leu Leu His
Leu Asn Ser Leu Phe Gly Lys Asp Gln;

(b) a peptide composition comprising one or more HIV-1 peptides; and (c) reagents for the detection of antigen-antibody complex formation between said one or more peptides and antibodies present in said biological sample.

7. The kit of claim 6, further comprising a peptide composition having one or more peptides selected from the group consisting of external env glycoprotein of HIV-2 and transmembrane env protein of HIV-2.

8. The kit of claim 6, wherein said one or more peptides of HIV-1 is selected from the group consisting of p25, p18, gp110, and gp41 of HIV-1.

9. The kit according to any one of claims 6, 7, or 8, wherein said peptide or protein is labeled with a label selected from the group consisting of an enzyme label, a fluorescent label, and a radioactive label.

10. An in vitro diagnostic assay for the detection of antigens of human immunodeficiency virus type 1, type 2, or both types 1 and 2 in a biological sample, comprising:

(a) contacting the biological sample with one or more antibodies against an HIV-2 peptide selected from the group consisting of:

(1) an antibody specific for a peptide encoded by the HIV-2 gag gene, wherein said peptide comprises the following sequence:

Met Gly Ala Arg Asn Ser Val Leu Arg Gly Lys
Lys Ala Asp Glu Leu
Glu Arg Ile Arg Leu Arg Pro Gly Gly Lys Lys
Lys Tyr Arg Leu Lys
His Ile Val Trp Ala Ala Asn Lys Leu Asp Arg
Phe Gly Leu Ala Glu
Ser Leu Leu Glu Ser Lys Glu Gly Cys Gln Lys
Ile Leu Thr Val Leu

-continued

Asp Pro Met Val Pro Thr Gly Ser Glu Asn Leu
Lys Ser Leu Phe Asn
Thr Val Cys Val Ile Trp Cys Ile His Ala Glu
Glu Lys Val Lys Asp
Thr Glu Gly Ala Lys Gln Ile Val Arg Arg His
Leu Val Ala Glu Thr
Gly Thr Ala Glu Lys Met Pro Ser Thr Ser Arg
Pro Thr Ala Pro Ser
Ser Glu Lys Gly Gly Asn Tyr Pro Val Gln His
Val Gly Gly Asn Tyr
Thr His Ile Pro Leu Ser Pro Arg Thr Leu Asn
Ala Trp Val Lys Leu
Val Glu Glu Lys Lys Phe Gly Ala Glu Val Val
Pro Gly Phe Gln Ala
Leu Ser Glu Gly Cys Thr Pro Tyr Asp Ile Asn
Gln Met Leu Asn Cys
Val Gly Asp His Gln Ala Ala Met Gln Ile Ile
Arg Glu Ile Ile Asn
Glu Glu Ala Ala Glu Trp Asp Val Gln His Pro
Ile Pro Gly Pro Leu

Pro Ala Gly Gln Leu Arg Glu Pro Arg Gly Ser
Asp Ile Ala Gly Thr
Thr Ser Thr Val Glu Glu Gln Ile Gln Trp Met
Phe Arg Pro Gln Asn
Pro Val Pro Val Gly Asn Ile Tyr Arg Arg Trp
Ile Gln Ile Gly Leu
Gln Lys Cys Val Arg Met Tyr Asn Pro Thr Asn
Ile Leu Asp Ile Lys
Gln Gly Pro Lys Glu Pro Phe Gln Ser Tyr Val
Asp Arg Phe Tyr Lys
Ser Leu Arg Ala Glu Gln Thr Asp Pro Ala Val
Lys Asn Trp Met Thr
Gln Thr Leu Leu Val Gln Asn Ala Asn Pro Asp
Cys Lys Leu Val Leu
Lys Gly Leu Gly Met Asn Pro Thr Leu Glu Glu
Met Leu Thr Ala Cys
Gln Gly Val Gly Gly Pro Gly Gln Lys Ala Arg
Leu Met Ala Glu Ala
Leu Lys Glu Val Ile Gly Pro Ala Pro Ile Pro
Phe Ala Ala Ala Gln

Gln Arg Lys Ala Phe Lys Cys Trp Asn Cys Gly
Lys Glu Gly His Ser
Ala Arg Gln Cys Arg Ala Pro Arg Arg Gln Gly
Cys Trp Lys Cys Gly
Lys Pro Gly His Ile Met Thr Asn Cys Pro Asp
Arg Gln Ala Gly Phe
Leu Gly Leu Gly Pro Trp Gly Lys Lys Pro Arg
Asn Phe Pro Val Ala
Gln Val Pro Gln Gly Leu Thr Pro Thr Ala Pro
Pro Val Asp Pro Ala
Val Asp Leu Leu Glu Lys Tyr Met Gln Gln Gly
Lys Arg Gln Arg Glu
Gln Arg Glu Arg Pro Tyr Lys Glu Val Thr Glu
Asp Leu Leu His Leu
Glu Gln Gly Glu Thr Pro Tyr Arg Glu Pro Pro
Thr Glu Asp Leu Leu
His Leu Asn Ser Leu Phe Gly Lys Asp Gln;

(2) an antibody specific for a peptide encoded by the HIV-2 env gene, wherein said peptide comprises the following sequence:

Met Met Asn Gln Leu Leu Ile Ala Ile Leu Leu Ala Ser Ala Cys Leu
Val Tyr Cys Thr Gln Tyr Val Thr Val Phe Tyr Gly Val Pro Thr Trp
Lys Asn Ala Thr Thr Pro Leu Phe Cys Ala Thr Arg Asn Arg Asp Thr
Trp Gly Thr Ile Gln Cys Leu Pro Asp Asn Asp Asp Tyr Gln Glu Ile
Thr Leu Asn Val Thr Glu Ala Phe Asp Ala Trp Asn Asn Thr Val Thr
Glu Gln Ala Ile Glu Asp Val Trp His Leu Phe Glu Thr Ser Ile Lys
Pro Cys Val Lys Leu Thr Pro Leu Cys Val Ala Met Lys Cys Ser Ser
Thr Glu Ser Ser Thr Gly Asn Asn Thr Thr Ser Lys Ser Thr Ser Thr
Thr Thr Thr Thr Pro Thr Asp Gln Glu Gln Glu Ile Ser Glu Asp Thr
Pro Cys Ala Arg Ala Asp Asn Cys Ser Gly Leu Gly Glu Glu Glu Thr
Ile Asn Cys Gln Phe Asn Met Thr Gly leu Glu Arg Asp Lys Lys Lys

```
Gln  Tyr  Asn  Glu  Thr  Trp  Tyr  Ser  Lys  Asp  Val  Val  Cys  Glu  Thr  Asn
Asn  Ser  Thr  Asn  Gln  Thr  Gln  Cys  Tyr  Met  Asn  His  Cys  Asn  Thr  Ser
Val  Ile  Thr  Glu  Ser  Cys  Asp  Lys  His  Tyr  Trp  Asp  Ala  Ile  Arg  Phe
Arg  Tyr  Cys  Ala  Pro  Pro  Gly  Tyr  Ala  Leu  Leu  Arg  Cys  Asn  Asp  Thr
Asn  Tyr  Ser  Gly  Phe  Ala  Pro  Asn  Cys  Ser  Lys  Val  Val  Ala  Ser  Thr
Cys  Thr  Arg  Met  Met  Glu  Thr  Gln  Thr  Ser  Thr  Trp  Phe  Gly  Phe  Asn
Gly  Thr  Arg  Ala  Glu  Asn  Arg  Thr  Tyr  Ile  Tyr  Trp  His  Gly  Arg  Asp
Asn  Arg  Thr  Ile  Ile  Ser  Leu  Asn  Lys  Tyr  Tyr  Asn  Leu  Ser  Leu  His
Cys  Lys  Arg  Pro  Gly  Asn  Lys  Thr  Val  Lys  Gln  Ile  Met  Leu  Met  Ser
Gly  His  Val  Phe  His  Ser  His  Tyr  Gln  Pro  Ile  Asn  Lys  Arg  Pro  Arg
Gln  Ala  Trp  Cys  Trp  Phe  Lys  Gly  Lys  Trp  Lys  Asp  Ala  Met  Gln  Glu
Val  Lys  Glu  Thr  Leu  Ala  Lys  His  Pro  Arg  Tyr  Arg  Gly  Thr  Asn  Asp
Thr  Arg  Asn  Ile  Ser  Phe  Ala  Ala  Pro  Gly  Lys  Gly  Ser  Asp  Pro  Glu
Val  Ala  Tyr  Met  Trp  Thr  Asn  Cys  Arg  Gly  Glu  Phe  Leu  Tyr  Cys  Asn
Met  Thr  Trp  Phe  Leu  Asn  Trp  Ile  Glu  Asn  Lys  Thr  His  Arg  Asn  Tyr
Ala  Pro  Cys  His  Ile  Lys  Gln  Ile  Ile  Asn  Thr  Trp  His  Lys  Val  Gly
Arg  Asn  Val  Tyr  Leu  Pro  Pro  Arg  Glu  Gly  Glu  Leu  Ser  Cys  Asn  Ser
Thr  Val  Thr  Ser  Ile  Ile  Ala  Asn  Ile  Asp  Trp  Gln  Asn  Asn  Asn  Gln
Thr  Asn  Ile  Thr  Phe  Ser  Ala  Glu  Val  Ala  Glu  Leu  Tyr  Arg  Leu  Glu
Leu  Gly  Asp  Tyr  Lys  Leu  Val  Glu  Ile  Thr  Pro  Ile  Gly  Phe  Ala  Pro
Thr  Lys  Glu  Lys  Arg  Tyr  Ser  Ser  Ala  His  Gly  Arg  His  Thr  Arg  Gly
Val  Phe  Val  Leu  Gly  Phe  Leu  Gly  Phe  Leu  Ala  Thr  Ala  Gly  Ser  Ala
Met  Gly  Ala  Ala  Ser  Leu  Thr  Val  Ser  Ala  Gln  Ser  Arg  Thr  Leu  Leu
Ala  Gly  Ile  Val  Gln  Gln  Gln  Gln  Gln  Leu  Leu  Asp  Val  Val  Lys  Arg
Gln  Gln  Glu  Leu  Leu  Arg  Leu  Thr  Val  Trp  Gly  Thr  Lys  Asn  Leu  Gln
Ala  Arg  Val  Thr  Ala  Ile  Glu  Lys  Tyr (3) an antibody specific for a p16 peptide encoded by the HIV-2 gag gene, wherein said peptide comprises the following sequence:

Met Gly Ala Arg Asn Ser Val Leu Arg Gly Lys Lys Ala Asp Glu Leu
Glu Arg Ile Arg Leu Arg Pro Gly Gly Lys Lys Lys Tyr Arg Leu Lys
His Ile Val Trp Ala Ala Asn Lys Leu Asp Arg Phe Gly Leu Ala Glu
Ser Leu Leu Glu Ser Lys Glu Gly Cys Gln Lys Ile Leu Thr Val Leu
Asp Pro Met Val Pro Thr Gly Ser Glu Asn Leu Lys Ser Leu Phe Asn
Thr Val Cys Val Ile Trp Cys Ile His Ala Glu Glu Lys Val Lys Asp
Thr Glu Gly Ala Lys Gln Ile Val Arg Arg His Leu Val Ala Glu Thr
Gly Thr Ala Glu Lys Met Pro Ser Thr Ser Arg Pro Thr Ala Pro Ser
Ser Glu Lys Gly Gly Asn Thr;

(4) an antibody specific for a p26 peptide encoded by the HIV-2 gag gene, wherein said peptide comprises the following sequence:

Pro Val Gln His Val Gly Gly Asn Tyr Thr His Ile Pro Leu Ser Pro
Arg Thr Leu Asn Ala Trp Val Lys Leu Val Glu Glu Lys Lys Phe Gly
Ala Glu Val Val Pro Gly Phe Gln Ala Leu Ser Glu Gly Cys Thr Pro
Tyr Asp Ile Asn Gln Met Leu Asn Cys Val Gly Asp His Gln Ala Ala
Met Gln Ile Ile Arg Glu Ile Ile Asn Glu Glu Ala Ala Glu Trp Asp
Val Gln His Pro Ile Pro Gly Pro Leu Pro Ala Gly Gln Leu Arg Glu
Pro Arg Gly Ser Asp Ile Ala Gly Thr Thr Ser Thr Val Glu Glu Gln
Ile Gln Trp Met Phe Arg Pro Gln Asn Pro Val Pro Val Gly Asn Ile
Tyr Arg Arg Trp Ile Gln Ile Gly Leu Gln Lys Cys Val Arg Met Tyr
Asn Pro Thr Asn Ile Leu Asp Ile Lys Gln Gly Pro Lys Glu Pro Phe
Gln Ser Tyr Val Asp Arg Phe Tyr Lys Ser Leu Arg Ala Glu Gln Thr
Asp Pro Ala Val Lys Asn Trp Met Thr Gln Thr Leu Leu Val Gln Asn
Ala Asn Pro Asp Cys Lys Leu Val Leu Lys Gly Leu Gly Met Asn Pro
Thr Leu Glu Glu Met Leu Thr Ala Cys Gln Gly Val Gly Gly Pro Gly
Gln Lys Ala Arg Leu Met Ala Glu Ala Leu Lys Glu Val Ile Gly Pro
Ala Pro Ile Pro Phe Ala Ala Ala Gln Gln; and (5) an antibody specific for a p12 peptide encoded by the HIV-2 gag gene, wherein said peptide comprises the following sequence:

Arg Lys Ala Phe Lys Cys Trp Asn Cys Gly Lys Glu Gly His Ser Ala
Arg Gln Cys Arg Ala Pro Arg Arg Gln Gly Cys Trp Lys Cys Gly Lys
Pro Gly His Ile Met Thr Asn Cys Pro Asp Arg Gln Ala Gly Phe Leu
Gly Leu Gly Pro Trp Gly Lys Lys Pro Arg Asn Phe Pro Val Ala Gln
Val Pro Gln Gly Leu Thr Pro Thr Ala Pro Pro Val Asp Pro Ala Val
Asp Leu Leu Glu Lys Tyr Met Gln Gln Gly Lys Arg Gln Arg Glu Gln
Arg Glu Arg Pro Tyr Lys Glu Val Thr Glu Asp Leu Leu His Leu Glu

-continued

Gln Gly Glu Thr Pro Tyr Arg Glu Pro Pro Thr Glu Asp Leu Leu His

Leu Asn Ser Leu Phe Gly Lys Asp Gln;

(b) contacting said biological sample with one or more antibodies specific for an HIV-1 peptide; and (c) detecting the formation of antigen-antibody complexes between said one or more antibodies and antigens present in said biological sample.

11. The assay of claim 10, wherein said sample is also contacted with one or more antibodies selected from the group consisting of antibody specific for the external HIV-2 env glycoprotein and antibody specific for the transmembrane HIV-2 env protein.

12. The assay of claim 10, wherein said one or more antibodies specific for an HIV-1 peptide are selected from the group consisting of antibody specific for HIV-1 p25, antibody specific for HIV-1 p18, antibody specific for HIV-1 gp110, and antibody specific for HIV-1 gp41.

13. The assay according to any one of claims 10, 11, and 12, wherein the formation of antigen-antibody complex is detected by employing a process selected from the group consisting of radioimmunoassay, radioimmunoprecipitation assay, immunofluorescence assay, enzyme-linked immunosorbent assay, and Western blot.

14. An in vitro diagnostic kit for the detection of antigens of a human immunodeficiency virus type 1, type 2, or both types 1 and 2 in a biological sample, comprising:

(a) an antibody composition comprising one or more antibodies specific for an HIV-2 peptide selected from the group consisting of:

(1) an antibody specific for a peptide encoded by the HIV-2 gag gene, wherein said peptide comprises the following sequence:

Met Gly Ala Arg Asn Ser Val Leu Arg Gly Lys

Lys Ala Asp Glu Leu

Glu Arg Ile Arg Leu Arg Pro Gly Gly Lys Lys

Lys Tyr Arg Leu Lys

His Ile Val Trp Ala Ala Asn Lys Leu Asp Arg

Phe Gly Leu Ala Glu

Ser Leu Leu Glu Ser Lys Glu Gly Cys Gln Lys

Ile Leu Thr Val Leu

Asp Pro Met Val Pro Thr Gly Ser Glu Asn Leu

Lys Ser Leu Phe Asn

Thr Val Cys Val Ile Trp Cys Ile His Ala Glu

Glu Lys Val Lys Asp

-continued

Thr Glu Gly Ala Lys Gln Ile Val Arg Arg His

Leu Val Ala Glu Thr

Gly Thr Ala Glu Lys Met Pro Ser Thr Ser Arg

Pro Thr Ala Pro Ser

Ser Glu Lys Gly Gly Asn Tyr Pro Val Gln His

Val Gly Gly Asn Tyr

Thr His Ile Pro Leu Ser Pro Arg Thr Leu Asn

Ala Trp Val Lys Leu

Val Glu Glu Lys Lys Phe Gly Ala Glu Val Val

Pro Gly Phe Gln Ala

Leu Ser Glu Gly Cys Thr Pro Tyr Asp Ile Asn

Gln Met Leu Asn Cys

Val Gly Asp His Gln Ala Ala Met Gln Ile Ile

Arg Glu Ile Ile Asn

Glu Glu Ala Ala Glu Trp Asp Val Gln His Pro

Ile Pro Gly Pro Leu

Pro Ala Gly Gln Leu Arg Glu Pro Arg Gly Ser

Asp Ile Ala Gly Thr

Thr Ser Thr Val Glu Glu Gln Ile Gln Trp Met

Phe Arg Pro Gln Asn

Pro Val Pro Val Gly Asn Ile Tyr Arg Arg Trp

Ile Gln Ile Gly Leu

Gln Lys Cys Val Arg Met Tyr Asn Pro Thr Asn

Ile Leu Asp Ile Lys

Gln Gly Pro Lys Glu Pro Phe Gln Ser Tyr Val

Asp Arg Phe Tyr Lys

-continued

| | | | | | | | | | |
|---|---|---|---|---|---|---|---|---|---|
| Ser | Leu | Arg | Ala | Glu | Gln | Thr | Asp | Pro | Ala | Val |
| | | | | | Lys | Asn | Trp | Met | Thr |
| Gln | Thr | Leu | Leu | Val | Gln | Asn | Ala | Asn | Pro | Asp |
| | | | | | Cys | Lys | Leu | Val | Leu |
| Lys | Gly | Leu | Gly | Met | Asn | Pro | Thr | Leu | Glu | Glu |
| | | | | | Met | Leu | Thr | Ala | Cys |
| Gln | Gly | Val | Gly | Gly | Pro | Gly | Gln | Lys | Ala | Arg |
| | | | | | Leu | Met | Ala | Glu | Ala |
| Leu | Lys | Glu | Val | Ile | Gly | Pro | Ala | Pro | Ile | Pro |
| | | | | | Phe | Ala | Ala | Ala | Gln |
| Gln | Arg | Lys | Ala | Phe | Lys | Cys | Trp | Asn | Cys | Gly |
| | | | | | Lys | Glu | Gly | His | Ser |
| Ala | Arg | Gln | Cys | Arg | Ala | Pro | Arg | Arg | Gln | Gly |
| | | | | | Cys | Trp | Lys | Cys | Gly |
| Lys | Pro | Gly | His | Ile | Met | Thr | Asn | Cys | Pro | Asp |

-continued

|

-continued

| | | | | | | | | | | | | | |
|---|---|---|---|---|---|---|---|---|---|---|---|---|---|
| Asn | Arg | Thr | Ile | Ile | Ser | Leu | Asn | Lys | Tyr | Tyr | Asn | Leu | Ser | Leu | His |
| Cys | Lys | Arg | Pro | Gly | Asn | Lys | Thr | Val | Lys | Gln | Ile | Met | Leu | Met | Ser |
| Gly | His | Val | Phe | His | Ser | His | Tyr | Gln | Pro | Ile | Asn | Lys | Arg | Pro | Arg |
| Gln | Ala | Trp | Cys | Trp | Phe | Lys | Gly | Lys | Trp | Lys | Asp | Ala | Met | Gln | Glu |
| Val | Lys | Glu | Thr | Leu | Ala | Lys | His | Pro | Arg | Tyr | Arg | Gly | Thr | Asn | Asp |
| Thr | Arg | Asn | Ile | Ser | Phe | Ala | Ala | Pro | Gly | Lys | Gly | Ser | Asp | Pro | Glu |
| Val | Ala | Tyr | Met | Trp | Thr | Asn | Cys | Arg | Gly | Glu | Phe | Leu | Tyr | Cys | Asn |
| Met | Thr | Trp | Phe | Leu | Asn | Trp | Ile | Glu | Asn | Lys | Thr | His | Arg | Asn | Tyr |
| Ala | Pro | Cys | His | Ile | Lys | Gln | Ile | Ile | Asn | Thr | Trp | His | Lys | Val | Gly |
| Arg | Asn | Val | Tyr | Leu | Pro | Pro | Arg | Glu | Gly | Glu | Leu | Ser | Cys | Asn | Ser |
| Thr | Val | Thr | Ser | Ile | Ile | Ala | Asn | Ile | Asp | Trp | Gln | Asn | Asn | Asn | Gln |
| Thr | Asn | Ile | Thr | Phe | Ser | Ala | Glu | Val | Ala | Glu | Leu | Tyr | Arg | Leu | Glu |
| Leu | Gly | Asp | Tyr | Lys | Leu | Val | Glu | Ile | Thr | Pro | Ile | Gly | Phe | Ala | Pro |
| Thr | Lys | Glu | Lys | Arg | Tyr | Ser | Ser | Ala | His | Gly | Arg | His | Thr | Arg | Gly |
| Val | Phe | Val | Leu | Gly | Phe | Leu | Gly | Phe | Leu | Ala | Thr | Ala | Gly | Ser | Ala |
| Met | Gly | Ala | Ala | Ser | Leu | Thr | Val | Ser | Ala | Gln | Ser | Arg | Thr | Leu | Leu |
| Ala | Gly | Ile | Val | Gln | Gln | Gln | Gln | Leu | Leu | Asp | Val | Val | Lys | Arg |
| Gln | Gln | Glu | Leu | Leu | Arg | Leu | Thr | Val | Trp | Gly | Thr | Lys | Asn | Leu | Gln |
| Ala | Arg | Val | Thr | Ala | Ile | Glu | Lys | Tyr | Leu | Gln | Asp | Gln | Ala | Arg | Leu |
| Asn | Ser | Trp | Gly | Cys | Ala | Phe | Arg | Gln | Val | Cys | His | Thr | Thr | Val | Pro |
| Trp | Val | Asn | Asp | Ser | Leu | Ala | Pro | Asp | Trp | Asp | Asn | Met | Thr | Trp | Gln |
| Glu | Trp | Glu | Lys | Gln | Val | Arg | Tyr | Leu | Glu | Ala | Asn | Ile | Ser | Lys | Ser |
| Leu | Glu | Gln | Ala | Gln | Ile | Gln | Gln | Glu | Lys | Asn | Met | Tyr | Gl

Ser Leu Leu Glu Ser Lys Glu Gly Cys Gln Lys Ile Leu Thr Val Leu

Asp Pro Met Val Pro Thr Gly Ser Glu Asn Leu Lys Ser Leu Phe Asn

Thr Val Cys Val Ile Trp Cys Ile His Ala Glu Glu Lys Val Lys Asp

Thr Glu Gly Ala Lys Gln Ile Val Arg Arg His Leu Val Ala Glu Thr

Gly Thr Ala Glu Lys Met Pro Ser Thr Ser Arg Pro Thr Ala Pro Ser

Ser Glu Lys Gly Gly Asn Tyr;

(4) an antibody specific for a p26 peptide encoded by the HIV-2 gag gene, wherein said peptide comprises the following sequence:

Pro Val Gln His Val Gly Gly Asn Tyr Thr His Ile Pro Leu Ser Pro

Arg Thr Leu Asn Ala Trp Val Lys Leu Val Glu Glu Lys Lys Phe Gly

Ala Glu Val Val Pro Gly Phe Gln Ala Leu Ser Glu Gly Cys Thr Pro

Tyr Asp Ile Asn Gln Met Leu Asn Cys Val Gly Asp His Gln Ala Ala

Met Gln Ile Ile Arg Glu Ile Ile Asn Glu Glu Ala Ala Glu Trp Asp

Val Gln His Pro Ile Pro Gly Pro Leu Pro Ala Gly Gln Leu Arg Glu

Pro Arg Gly Ser Asp Ile Ala Gly Thr Thr Ser Thr Val Glu Glu Gln

Ile Gln Trp Met Phe Arg Pro Gln Asn Pro Val Pro Val Gly Asn Ile

Tyr Arg Arg Trp Ile Gln Ile Gly Leu Gln Lys Cys Val Arg Met Tyr

Asn Pro Thr Asn Ile Leu Asp Ile Lys Gln Gly Pro Lys Glu Pro Phe

Gln Ser Tyr Val Asp Arg Phe Tyr Lys Ser Leu Arg Ala Glu Gln Thr

Asp Pro Ala Val Lys Asn Trp Met Thr Gln Thr Leu Leu Val Gln Asn

Ala Asn Pro Asp Cys Lys Leu Val Leu Lys Gly Leu Gly Met Asn Pro

Thr Leu Glu Glu Met Leu Thr Ala Cys Gln Gly Val Gly Gly Pro Gly

Gln Lys Ala Arg Leu Met Ala Glu Ala Leu Lys Glu Val Ile Gly Pro

Ala Pro Ile Pro Phe Ala Ala Ala Gln Gln; and (5) an antibody specific for a p12 peptide encoded by the HIV-2 gag gene, wherein said peptide comprises the following sequence:

Arg Lys Ala Phe Lys Cys Trp Asn Cys Gly Lys Glu Gly His Ser Ala

Arg Gln Cys Arg Ala Pro Arg Arg Gln Gly Cys Trp Lys Cys Gly Lys

Pro Gly His Ile Met Thr Asn Cys Pro Asp Arg Gln Ala Gly Phe Leu

Gly Leu Gly Pro Trp Gly Lys Lys Pro Arg Asn Phe Pro Val Ala Gln

Val Pro Gln Gly Leu Thr Pro Thr Ala Pro Pro Val Asp Pro Ala Val

Asp Leu Leu Glu Lys Tyr Met Gln Gln Gly Lys Arg Gln Arg Glu Gln

Arg Glu Arg Pro Tyr Lys Glu Val Thr Glu Asp Leu Leu His Leu Glu

Gln Gly Glu Thr Pro Tyr Arg Glu Pro Pro Thr Glu Asp Leu Leu His

Leu Asn Ser Leu Phe Gly Lys Asp Gln;

(b) an antibody composition comprising one or more antibodies specific for an HIV-1 peptide; and (c) reagents for the detection of antigen-antibody complex formation between said one or more antibodies and antigens present in said biological sample.

15. The kit of claim 14, further comprising an antibody composition having one or more antibodies selected from the group consisting of antibody specific for the HIV-2 external env glycoprotein and antibody specific for the HIV-2 transmembrane env protein.

16. The kit of claim 14, wherein said one or more antibodies specific for an HIV-1 peptide are selected from the group consisting of antibody specific for HIV-1 p25, antibody specific for HIV-1 p18, antibody specific for HIV-1 gp110, and antibody specific for HIV-1 gp41.

17. The diagnostic assay of any one of claims 1–5, wherein said HIV-2 peptides and proteins are specific for HIV-$2_{ROD}$ and wherein said HIV-1 peptides are specific for HIV-$1_{BRU}$.

18. The diagnostic kit of any one of claims 6–9, wherein said HIV-2 peptides and proteins are specific for HIV-$2_{ROD}$ and wherein said HIV-1 peptides are specific for HIV-$1_{BRU}$.

19. The diagnostic assay of any one of claims 10–12, wherein said HIV-2 peptides and proteins are specific for HIV-$2_{ROD}$ and wherein said HIV-1 peptides are specific for HIV-$1_{BRU}$.

20. The diagnostic assay of any one of claims 14–16, wherein said HIV-2 peptides and proteins are specific for HIV-$2_{ROD}$ and wherein said HIV-1 peptides are specific for HIV-$1_{BRU}$.

21. The diagnostic assay of claim 1, wherein said contacting steps occur simultaneously.

22. The diagnostic assay of claim 6, wherein said contacting steps occur simultaneously.

23. The diagnostic assay of claim 10, wherein said contacting steps occur simultaneously.

24. The diagnostic assay of claim 14, wherein said contacting steps occur simultaneously.

* * * * *

UNITED STATES PATENT AND TRADEMARK OFFICE
CERTIFICATE OF CORRECTION

PATENT NO. : 5,830,641

DATED : November 3, 1998

INVENTOR(S) : MONTAGNIER et al.

It is certified that error appears in the above-indentified patent and that said Letters Patent is hereby corrected as shown below:

In the Title, Block [54], delete the title in its entirety and insert the following:

--METHODS AND KITS FOR DETECTING HUMAN IMMUNODEFICIENCY VIRUS TYPE 1 AND TYPE 2 (HIV-1 AND HIV-2)--.

Claim 1, col. 45, line 5, after "Gln Leu Ile Arg Leu Leu Thr Arg", insert the following:

--Leu Tyr Ser Ile Cys Arg Asp Leu Leu Ser Arg Ser Phe Leu Thr Leu--.

Claim 6, col. 48, line 23, "both type" should read --both types--.

Claim 10, col. 61, line 18 (last line of (3)), "Thr" should read --Tyr--.

Signed and Sealed this

Nineteenth Day of October, 1999

*Attest:*

Q. TODD DICKINSON

*Attesting Officer*   *Acting Commissioner of Patents and Trademarks*